(12) United States Patent
Ko

(10) Patent No.: US 12,268,630 B2
(45) Date of Patent: Apr. 8, 2025

(54) ENERGY TRANSMISSION MODULE FOR VAGINAL CANAL TREATMENT APPARATUS, METHOD FOR CONTROLLING SAME, AND TREATMENT METHOD USING SAME

(71) Applicant: LUTRONIC CORPORATION, Goyang (KR)

(72) Inventor: Kwang Chon Ko, Paju (KR)

(73) Assignee: LUTRONIC CORPORATION, Goyang (KR)

( * ) Notice: Subject to any disclaimer, the term of this patent is extended or adjusted under 35 U.S.C. 154(b) by 789 days.

(21) Appl. No.: 17/294,331

(22) PCT Filed: Oct. 7, 2019

(86) PCT No.: PCT/KR2019/013106
§ 371 (c)(1),
(2) Date: May 14, 2021

(87) PCT Pub. No.: WO2020/101175
PCT Pub. Date: May 22, 2020

(65) Prior Publication Data
US 2022/0008248 A1    Jan. 13, 2022

(30) Foreign Application Priority Data
Nov. 16, 2018  (KR) .................. 10-2018-0142052

(51) Int. Cl.
A61F 7/12    (2006.01)
A61F 7/00    (2006.01)

(52) U.S. Cl.
CPC ............... *A61F 7/12* (2013.01); *A61F 7/007* (2013.01); *A61F 2007/005* (2013.01);
(Continued)

(58) Field of Classification Search
CPC ......... A61B 18/00; A61B 18/08; A61B 18/12; A61B 18/1206; A61B 18/14;
(Continued)

(56) References Cited

U.S. PATENT DOCUMENTS 5,443,470 A    8/1995   Stern et al.
9,814,408 B2   11/2017  Mabary et al.
(Continued)

FOREIGN PATENT DOCUMENTS

JP     3566722 B2     9/2004
JP     2013510640 A   3/2013
(Continued)

*Primary Examiner* — Tigist S Demie

(57) ABSTRACT

The present invention relates to an energy transmission module for a vaginal canal treatment apparatus, a method for controlling same, and a treatment method using same according to the present invention allow transmission of energy by means of insertion into the vaginal canal and expansion of the vaginal canal, and thus allow treatment by selectively or complexly generating denaturation such as coagulation and ablation over a large area in a short time, allow one-shot treatment, and allow treatment of an area with folds. Therefore, the efficiency and accuracy of the treatment can be enhanced. Since the tissue in the vaginal canal can be treated even without a surgical operation, user's pain and discomfort can be minimized.

19 Claims, 49 Drawing Sheets

(52) U.S. Cl.
CPC .............. *A61F 2007/0071* (2013.01); *A61F 2007/0086* (2013.01); *A61F 2007/0096* (2013.01)

(58) Field of Classification Search
CPC ........ A61B 18/1485; A61B 2018/0016; A61B 2018/0022; A61B 2018/00559; A61B 2018/00577; A61B 2018/00702; A61B 2018/00761; A61B 2018/00779; A61B 2018/00791; A61B 2018/00797; A61B 2018/00886; A61B 2018/126; A61B 2018/1467; A61F 2007/005; A61F 2007/0071; A61F 2007/0086; A61F 2007/0096; A61F 7/007; A61F 7/12
See application file for complete search history.

(56) References Cited

U.S. PATENT DOCUMENTS

| | | | | |
|---|---|---|---|---|
| 2004/0006337 | A1* | 1/2004 | Nasab | A61B 18/1206 606/41 |
| 2008/0188912 | A1* | 8/2008 | Stone | A61F 7/12 606/192 |
| 2008/0319350 | A1* | 12/2008 | Wallace | A61B 5/0538 606/41 |
| 2010/0125268 | A1 | 5/2010 | Gustus et al. | |
| 2011/0178584 | A1 | 7/2011 | Parmer et al. | |
| 2012/0265044 | A1 | 10/2012 | Broens | |
| 2013/0165916 | A1 | 6/2013 | Mathur et al. | |
| 2014/0330178 | A1 | 11/2014 | Peddicord | |
| 2015/0119882 | A1 | 4/2015 | Cao et al. | |
| 2015/0190195 | A1* | 7/2015 | Hanson | A61B 18/1492 606/41 |
| 2017/0042615 | A1* | 2/2017 | Salahieh | A61B 5/01 |
| 2018/0055563 | A1* | 3/2018 | Shetake | A61B 5/4325 |

FOREIGN PATENT DOCUMENTS

| | | |
|---|---|---|
| JP | 2016534842 A | 11/2016 |
| JP | 6130397 B2 | 5/2017 |
| KR | 20110104504 A | 9/2011 |
| KR | 20120100921 A | 9/2012 |
| WO | WO2012075112 A1 | 6/2012 |

* cited by examiner

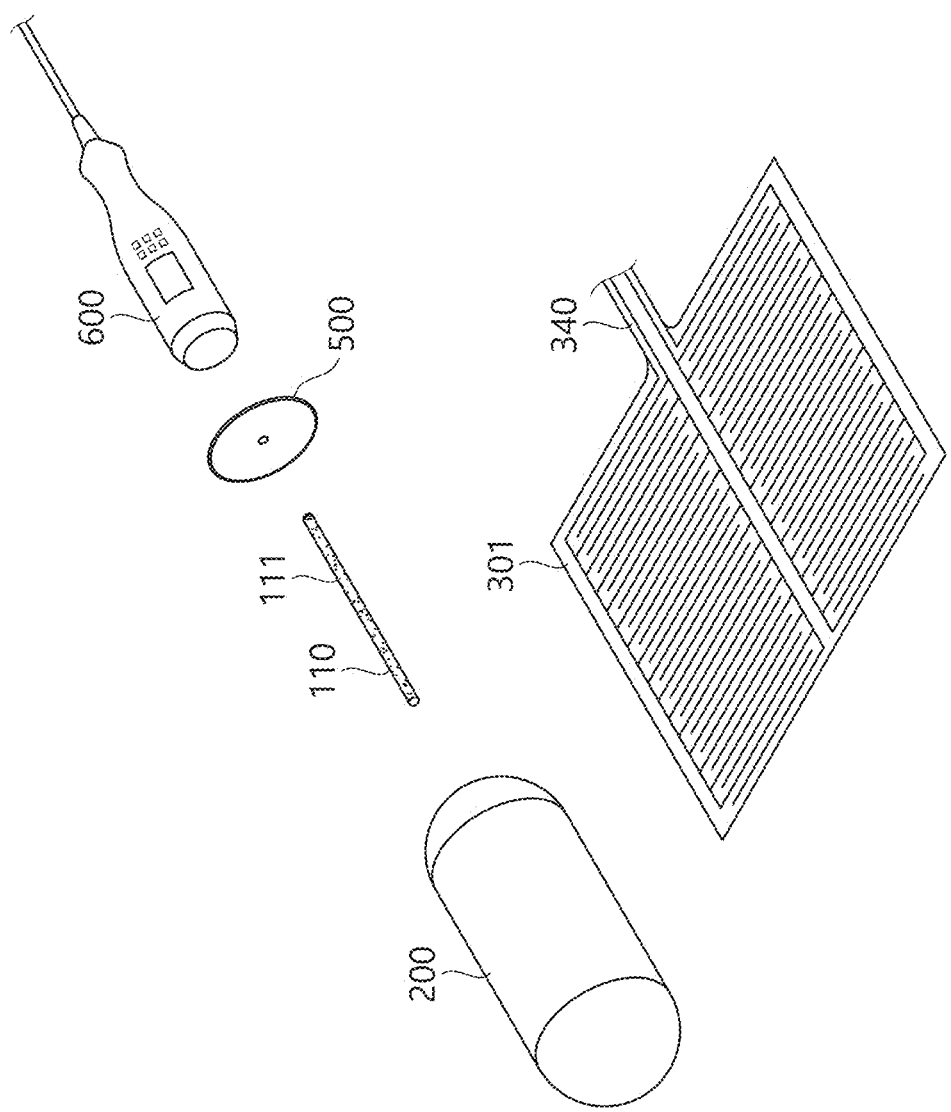

FIG. 38
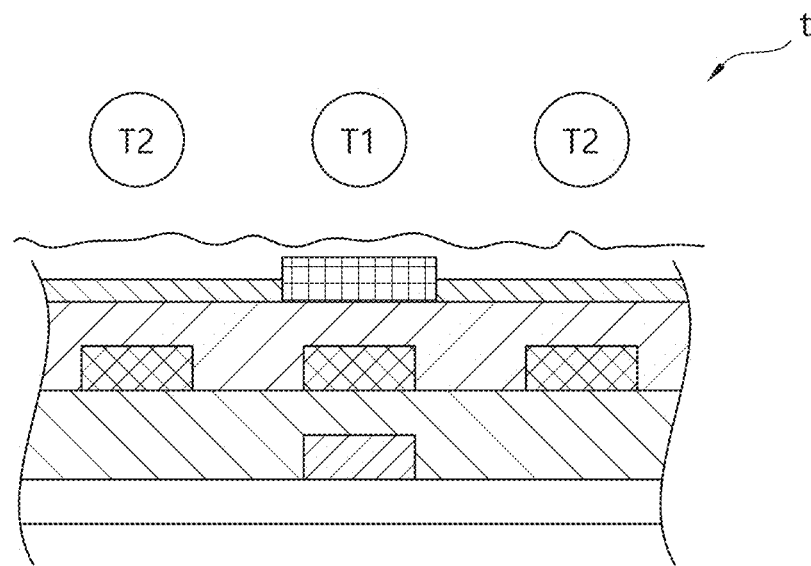
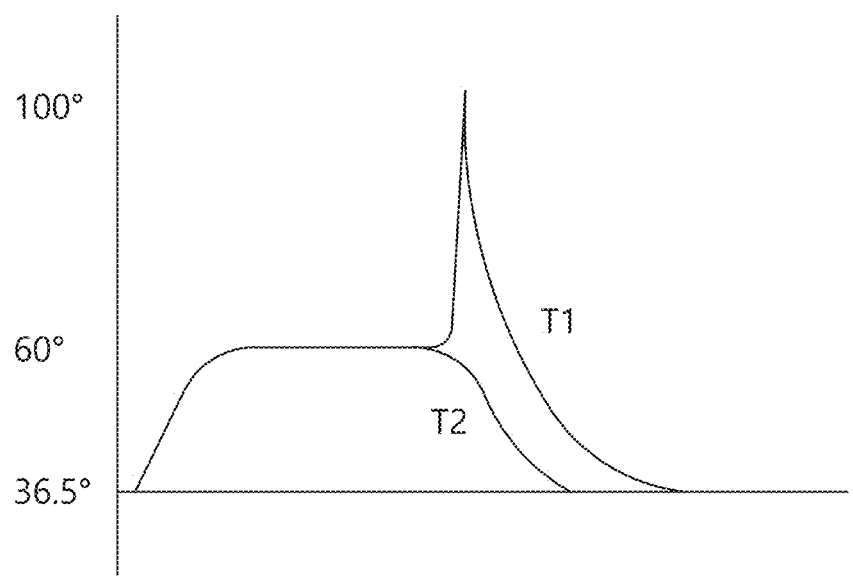

ENERGY TRANSMISSION MODULE FOR VAGINAL CANAL TREATMENT APPARATUS, METHOD FOR CONTROLLING SAME, AND TREATMENT METHOD USING SAME

TECHNICAL FIELD

The disclosure relates to an energy transfer module for a vaginal-canal treatment device, a control method thereof, and a treatment method using the same, and more particularly to a vaginal-canal treatment device using energy to treat tissue in a vaginal canal.

BACKGROUND ART

As a part of female genitalia, a vaginal canal (vagina) is decreased in elasticity of a vagina inner-wall due to delivery or aging, and is in particular suddenly stretched when giving birth. The stretched vagina inner-wall returns to some extent after the delivery but its elasticity is rarely restored to that of before the delivery.

To help women to restore their satisfaction and confidence by treating the stretched vaginal canal, there have conventionally been used a surgical incision into the stretched part, implantation of a prosthesis, and the like surgical operations. Regarding such a related art, US patent publication No. US20050187429 has been disclosed.

However, the related art based on the surgical operation has had problems of complicated processes, patient's suffering, and serious side-effects.

DISCLOSURE

Technical Problem

In order to solve the problem, an object of the present disclosure is to provide an energy transfer module for a vaginal-canal treatment device, which is inserted in a vaginal canal, transfers energy and treats tissue when the tissue of the vaginal canal undergoes treatment, a control method thereof, and a treatment method using the same.

Technical Solution

In order to solve the above problems, an energy transfer module for vaginal canal treatment is provided including: a flexible substrate configured to be transformed as an expansion portion for enlarging a vaginal canal is expanded; and a heating electrode provided in the substrate and configured to generate heat and heat the vaginal canal.

The heating electrode may be configured to generate heat throughout a surface.

Further, the heating electrode may include a plurality of heating electrodes, may be provided in each individual region divided on a plane of the substrate, and may be configured to independently heat each individual region.

Further, the heating electrode may be configured to receive alternating current (AC) power and generate heat.

Moreover, the energy transfer module may further include a temperature sensor configured to measure temperature corresponding to heating of the heating electrode.

Meanwhile, the flexible substrate may include an insulating first layer and an insulating second layer which are in at least partially contact with the vaginal canal, and the plurality of heating electrodes may be provided between the first layer and the second layer.

Meanwhile, the temperature sensor may be provided in the second layer.

In addition, a method of controlling an energy transfer module for vaginal canal treatment is provided including: applying power to generate heat from a heating electrode provided in a substrate being in contact with a vagina inner-wall as an expansion portion is expanded; and controlling power to maintain the vagina inner-wall at a set temperature for a set period of time.

The heating electrode may be configured to generate heat throughout a surface, the heating electrode may include a plurality of heating electrodes which are respectively provided in a plurality of regions divided from the substrate, and the applying of the power may include applying power to a heating region selected among the plurality of divided regions based on a preset mode or a user's input.

Meanwhile, the applying of the power may include controlling power by feeding back a temperature measurement value from a temperature sensor provided in the substrate.

Further, the applying of the power may include performing pulse width modulation (PWM) by feeding back the temperature measurement value.

Moreover, the applying of the power may include adjusting voltage of the power by feeding back the temperature measurement value.

Further, the applying of the power may include controlling the power to maintain the temperature measurement value at a set temperature of 40° C. to 70° C.

In addition, a vaginal-canal treatment method using an energy transfer module for vaginal canal treatment is provided including: enlarging a vaginal canal by inserting a treatment device including a heating electrode into an opening of the vaginal canal; treating tissue by heating an inner wall of the enlarged vaginal canal with the heating electrode; and removing the treatment device.

The treating of the tissue may be performed by transferring thermal energy from a surface heating electrode to the inner wall of the vaginal canal.

Further, the treating of the tissue may be performed by heating at least a part divided from a treatment region of the vagina inner-wall.

Moreover, the treating of the tissue may include maintaining the treatment region at 40° C. to 60° C. for a predetermined period of time.

Further the treating of the tissue may include causing coagulation denaturation in tissue of a treatment region.

In addition, an energy transfer module for vaginal canal treatment is provided including: a flexible substrate configured to be transformed as an expansion portion for enlarging a vaginal canal may be expanded; and a plurality of radio frequency (RF) electrodes provided in the substrate and configured to transfer RF energy to the vaginal canal at a plurality of points.

The flexible substrate may include an insulating first layer to be in at least partially contact with the vaginal canal; and an insulating second layer, and the plurality of RF electrodes may be exposed at the plurality of points on an outer surface of the first layer.

Meanwhile, the plurality of RF electrodes may be configured to be in contact with the vagina inner-wall.

Further, the plurality of RF electrodes may include a smooth outer surface not to be inserted in the vagina inner-wall.

Meanwhile, the plurality of RF electrodes may be provided in a region divided from a plane of the substrate, and each divided region may be configured to independently apply RF energy.

Moreover, the plurality of RF electrodes may include a monopolar type or a bipolar type.

Further, the plurality of RF electrodes may include the bipolar type, and at least one of RF electrodes adjacent to a certain RF electrode has opposite polarity.

Meanwhile, the energy transfer module may further include a temperature sensor provided adjacent to the RF electrode, and configured to measure temperature.

In addition, a method of controlling an energy transfer module for vaginal canal treatment is provided including: applying radio frequency (RF) energy in a state that an RF electrode provided on a substrate transformed as an expansion portion may be expanded may be in contact with a vagina inner-wall; and blocking the RF energy when temperature of the vagina inner-wall may be raised up to a set temperature.

The RF electrode may include a plurality of RF electrodes which may be respectively provided in a plurality of regions divided from the substrate, and the applying of the RF energy may include applying power to a RF-energy applying region selected among the plurality of divided regions based on a preset mode or a user's input.

Further, the blocking of the RF energy may include controlling the power by feeding back a temperature measurement value from a temperature sensor provided in the substrate.

Moreover, the applying of the RF energy may include applying monopolar or bipolar energy to the RF electrode.

Further, the applying of the RF energy may be performed by adjusting RF power and an applying time within a range of the temperature measurement value from 60° C. to 100° C.

In addition, a vaginal-canal treatment method using an energy transfer module for vaginal canal treatment is provided including: enlarging a vaginal canal by inserting a treatment device including a radio frequency (RF) electrode into an opening of the vaginal canal; treating tissue by transferring RF energy based on contact between the RF electrode and an inner wall of the enlarged vaginal canal; and removing the treatment device.

The treating of the tissue may include causing denaturation in at least a part of tissue of the vagina inner-wall by transferring the RF energy from the RF electrode.

Further, the treating of the tissue may be performed by transferring the RF energy to a plurality of spaced points in the vaginal inner-wall.

Moreover, the treating of the tissue may include causing ablation denaturation in an at least partial region of the vaginal inner-wall by transferring the RF energy.

Further, the treating of the tissue may include denaturing the tissue in a range where the temperature of the tissue to which the RF energy may be applied does not exceed 100° C.

In addition, an energy transfer module for vaginal canal treatment is provided including: a flexible substrate configured to be transformed as an expansion portion for enlarging a vaginal canal may be expanded; a heating electrode provided in the substrate and configured to generate heat and heat the vaginal canal; and a radio frequency (RF) electrode provided in the substrate and configured to transfer RF energy to the vaginal canal at a plurality of points.

The heating electrode may be configured to generate heat throughout a surface, may include a plurality of heating electrodes to respectively heat a plurality of heating regions divided from a plane of the substrate, and the RF electrode may include a plurality of RF electrodes, which may be configured to respectively apply RF energy to a plurality of RF-energy applying regions divided from the plane of the substrate.

Meanwhile, the heating region and the RF-energy applying region may be configured to at least partially include an overlapped region.

Meanwhile, the heating region and the RF-energy applying region may include the heating electrodes and the RF electrodes arrayed not to overlap.

Meanwhile, the flexible substrate may include an insulating first layer to be in at least partially contact with the vaginal canal; and an insulating second layer, and the heating electrode may be provided between the first layer and the second layer, and the RF electrode may be exposed at a plurality of points on an outer surface of the first layer.

Meanwhile, the energy transfer module may further include a temperature sensor provided in the second layer.

In addition, a method of controlling an energy transfer module for vaginal canal treatment is provided including: applying power to a surface heating electrode to generate heat from the heating electrode provided in a substrate being in contact with a vagina inner-wall as an expansion portion may be expanded; and controlling power applied to the heating electrode to maintain the vagina inner-wall at a predetermined temperature for a predetermined period of time; and applying a radio frequency (RF) energy to an RF electrode provided in the substrate and being in contact with the vagina inner-wall.

The applying of the power to the heating electrode and the applying of the RF energy may be selectively or simultaneously performed based on a user's input.

Meanwhile, the heating electrode and the RF electrode may include a plurality of heating electrodes and a plurality of RF electrodes to be respectively arranged in a plurality of regions divided from the substrate, and the applying of the power to the heating electrode and the applying of the RF energy may be performed with regard to at least some of the divided regions based on a preset mode or a user's input.

Further, the applying of the power to the heating electrode and the applying of the RF energy may be performed based on a temperature measurement value received from a plurality of temperature sensors provided in the substrate.

Here, the applying of the power to the heating electrode may include controlling a temperature to be maintained at 40° C. to 70° C. to enlarge a coagulation region in the vaginal canal.

Meanwhile, the applying of the RF energy may be performed by adjusting RF power and an applying time in a range where the temperature measurement value does not exceed 100° C.

In addition, a vaginal-canal treatment method using an energy transfer module for vaginal canal treatment is provided including: enlarging a vaginal canal by inserting a treatment device including a heating electrode and a radio frequency (RF) electrode into an opening of the vaginal canal; treating tissue based on heating by making the heating electrode generate heat and heating an inner wall of the enlarged vaginal canal; treating tissue based on RF energy transfer by transferring RF energy to the inner wall of the enlarged vaginal canal with the RF electrode; and removing the treatment device.

The treating of the tissue based on the heating and the treating of the tissue based on the RF energy transfer may be selectively or simultaneously performed based on a preset mode or a user's input.

Meanwhile, the treating of the tissue based on the heating and the treating of the tissue based on the RF energy transfer may be duplicatively performed in an at least partial region of the inner wall of the vaginal canal.

Further, the treating of the tissue based on the heating and the treating of the tissue based on the RF energy transfer may be respectively performed in separate regions of the inner wall of the vaginal canal.

Meanwhile, the treating of the tissue based on the heating may cause coagulation denaturation in the vagina inner-wall, and the treating of the tissue based on the RF energy transfer may cause ablation denaturation in the vagina inner-wall.

Advantageous Effects

As described above, the disclosure provides an energy transfer module for a vaginal-canal treatment device, a control method thereof, and a treatment method using the same, in which energy is transferred by insertion into a vaginal canal and enlargement of the vaginal canal to thereby perform treatment by selectively or complexly causing ablation and coagulation denaturation in a large area for a short period of time, and one-shot treatment is possible and wrinkled part can undergo the treatment to thereby improve the treatment in efficiency and accuracy. Further, the tissue in the vaginal canal is treatable without a surgical operation, thereby having an effect on minimizing a patient's suffering or discomfort.

DESCRIPTION OF DRAWINGS

FIG. 4 is an exploded perspective view of the handpiece.

FIG. 38 is a graph showing temperature profile corresponding to portions when electrode treatment is performed using the energy transfer module for the vaginal canal treatment of FIG. 32.

MODE FOR CARRYING OUT DISCLOSURE

Figure 1:
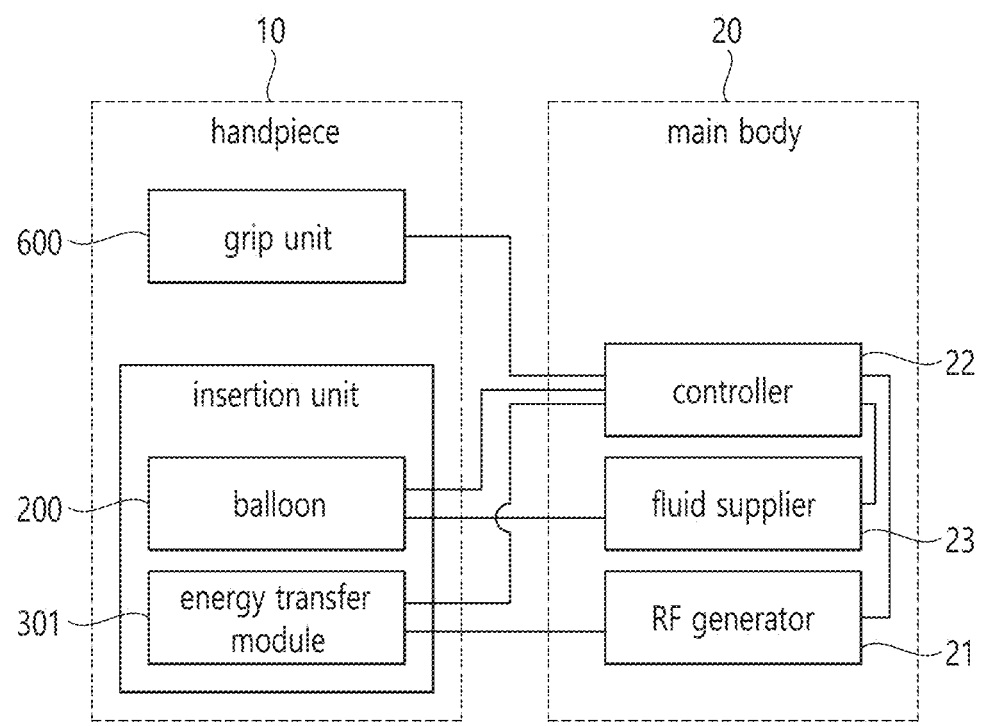
FIG. 1 is a block diagram showing elements according to a first embodiment of the disclosure.

Below, a vaginal-canal treatment device according to embodiments of the disclosure will be described in detail with reference to accompanying drawings. Elements described in the following embodiments may be called other names in relevant fields. However, if the elements are similar or identical in terms of their functions, they may be regarded as equivalents even in alternative embodiments. Further, signs assigned to the elements are given for convenience of description. However, content on the drawings with these given signs do not limit the elements to a range in the drawings. Likewise, even though the elements on the drawings are partially modified according to alternative embodiments, they having functional similarity and identity may be regarded as equivalents. Further, if those skilled in the art recognizes natural involvement of elements, descriptions of the elements will be omitted.

Below, tissue refers to a set of cells distributed in a vaginal canal of a human, the vaginal canal refers to a part connecting a uterus and a pudendum among female genitalia, and the inner wall or side of the vaginal canal refers to a surface with which the treatment device inserted in the vaginal canal is in contact.

Descriptions will be made on the assumption that the tissue includes a part or the whole of tissue distributed from a mucous membrane (or mucosa) of the vagina inner-wall up to a predetermined depth. Further, descriptions will be made on the assumption that treatment includes an action of doing tissue remodeling with thermal energy by transferring radio frequency (RF) energy to submucosal vaginal-tissue. For example, the treatment may be given for at least one of tightening, rejuvenation, laxity, lifting and tone and textural changes with regard to the inner wall of the vaginal canal.

FIG. 1 is a block diagram showing elements according to a first embodiment of the disclosure.

As shown therein, the vaginal-canal treatment device according to the disclosure may include a handpiece 10 and a main body 20.

The handpiece 10 is configured to transfer RF energy as inserted in the vaginal canal. The handpiece 10 may include an insertion unit 100 { 도면에 참조부호 없음 } to be inserted in the vaginal canal, and a grip unit 600.

The insertion unit 100 is configured to treat the tissue by transferring the RF energy in a state that the vaginal canal is enlarged as the insertion unit 100 is inserted in the vaginal canal. The insertion unit 100 is configured to expand and contract in response to a user's input, and configured to enlarge the vaginal canal during the expansion. When an expansion portion is expanded, an area of contact with the inner wall of the vaginal canal increases to thereby maximize a treatment area. The insertion unit 100 is configured to configured to treat the tissue by transferring energy in the state that the vaginal canal is enlarged. Further, the insertion unit 100 may include a temperature sensor 330 to measure temperature while proceeding with the treatment.

The grip unit 600 is configured to be gripped and used by a user, and supports the insertion unit 100 so that the user can insert the insertion unit 100 into the vaginal canal while gripping the grip unit 600. The grip unit 600 has a first side connected to a first end of the insertion unit 100, and a second side to receive fluid and energy from a fluid source and an energy source provided in the main body 20.

The grip unit 600 may include an input unit to transmit a user's input to a controller 22 when the user makes the input, or may include a display to monitor a condition of tissue and a state of treatment.

The main body 20 is configured to supply the energy and fluid required for the treatment, and configured to control general processes during the treatment.

The main body 20 may include an RF generator 21, a fluid supplier 23 and the controller 22. The RF generator 21 is configured to receive energy from the outside and generate RF energy. The RF generator 21 may be configured to generate the RF energy used for the treatment, in which the RF energy is different in frequency according to a constitution of a patient, composition of tissue, the size of the tissue, etc. For example, energy used in treating a vagina inner-wall t may be controlled within a range from 0.1 to 0.8 MHz.

The fluid supplier 23 is configured to supply the fluid to the insertion unit 100 and expand the insertion unit 100. The fluid supplier 23 may be configured to control the flow rate and pressure of the supplied fluid. Meanwhile, when the expansion portion of the insertion unit 100 is embodied by a balloon, the fluid supplier 23 is configured to supply liquid or gaseous expansion medium to the balloon. When the gaseous expansion medium is supplied, air in the atmosphere may be used and therefore there may be no need of a separate means for storing the expansion medium. The fluid supplier 23 may include a pump, a valve, etc. to supply the fluid and maintain the pressure, but descriptions about such elements will be omitted because they have been widely used.

The controller 22 is configured to perform general control for the treatment device including the RF generator 21 and the fluid supplier 23. The controller 22 may be configured to control the applying time, power, voltage, current, energy amount, and frequency of the RF energy generated in the RF generator 21. Further, the controller 22 may be configured to control the fluid supplying amount and pressure of the fluid supplier 23. The controller 22 may perform feedback control based on the temperature of the tissue measured by the temperature sensor 330 while controlling the RF generator 21, and perform fluid control through a pressure sensor and a flowmeter provided in the fluid supplier 23.

Although it is described by way of example that the treatment device in this embodiment employs the RF energy, various types of energy may be used as long as it can heat and treat the tissue.

Figure 2:
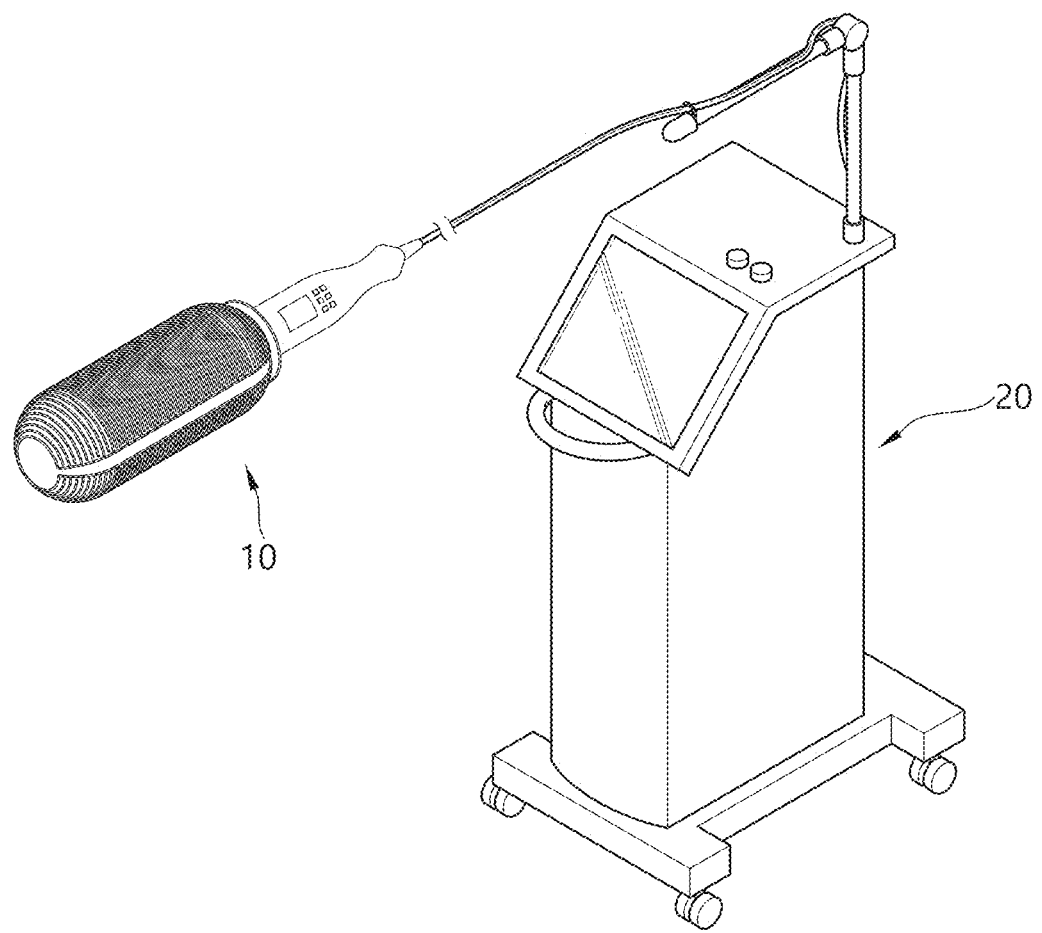
FIG. 2 is a perspective view according to the first embodiment of the disclosure.

FIG. 2 is a perspective view according to the first embodiment of the disclosure.

As described above, the first embodiment according to the disclosure may include the main body 20 and the handpiece 10. The main body 20 and the handpiece 10 are connected by a cable 30, and the cable 30 may include an RF cable, a fluid channel, and a feedback path. The handpiece 10 may include a connector at one side, to which the cable 30 is detachably connected.

Meanwhile, the main body 20 may externally include a power on/off switch, a frequency control lever for controlling the frequency of the RF energy generated in the RF generator, and a touch screen for displaying various pieces of information such as operation content of the treatment device, allowing a user to input a command, and displaying treatment information. The controller 22 may be configured to control the RF generator 21 and the fluid supplier 23 in a preset treatment mode, and control the RF generator 21 and the fluid supplier 23 based on a user's manual input for changing some variables in the treatment mode.

Below, the configuration and operations of the handpiece 10 according to the disclosure will be described in detail with reference to FIGS. 3 to 13.

Figure 3:
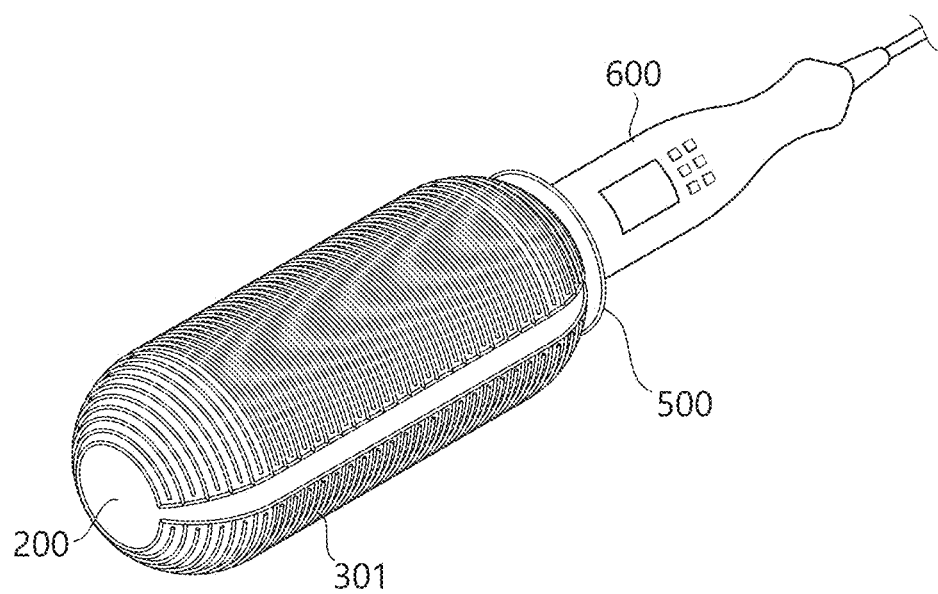
FIG. 3 is a perspective view of a handpiece.

FIG. 3 is a perspective view of the handpiece 10, and FIG. 4 is an exploded perspective view of the handpiece 10. As shown therein, the handpiece 10 includes the insertion unit 100 and the grip unit 600.

As described above, the insertion unit 100 is configured to be inserted into the vaginal canal from the outside through a vaginal opening. The insertion unit 100 is configured to expand in a state of being inserted in the vaginal canal and increase in diameter, and configured to enlarge the vaginal canal while supporting the vagina inner-wall t as the diameter of the insertion unit 100 is increased. The insertion unit 100 may include a shaft 110, a guide 500, a balloon 200 and an energy transferer 301.

The shaft 110 has a first side firmly connected to the grip unit 600 and is configured to firmly support the insertion unit 100 when the insertion unit 100 is inserted in the vaginal canal. The shaft 110 is configured to internally include a fluid channel through which the fluid can flow. The fluid channel has a first side connected to and fluid-communicating with the grip unit 600, and a second side formed with an outlet 111 for fluid-communicating with the balloon 200 surrounding the shaft 110. The shaft 110 may be provided to have a length corresponding to the length of the vaginal canal, and range from 2 cm to 15 cm because the length of the vaginal canal is variable depending on individuals. Further, the shaft 110 may be provided to have a diameter shorter than or equal to 3 cm to minimize feeing of irritation, suffering or discomfort when inserted into the contracted vaginal canal.

The guide 500 is put on the shaft 110 at a side of the grip unit 600, and supports the end of the balloon 200 to prevent the balloon 200 from expanding in an outward direction of the vaginal canal while the balloon 200 is expanding. At this time, a supporting force is mainly transferred in a lengthwise direction, thereby preventing outward expansion.

The balloon 200 is configured to expand so that the vaginal canal can be enlarged, and functions as the expansion portion. The balloon 200 is contracted to be inserted into the narrow vaginal canal when the insertion unit 100 is inserted into the vaginal canal, and expanded to treat a large area by increasing a contact area between the vagina inner-wall t and electrodes 320 (to be described later) when the RF energy is transferred. Taking an average size of a female vaginal canal into account, the balloon 200 is configured to have, but not limited to, a diameter of 2 cm during the contraction and a diameter of about 5-10 cm during the expansion.

The balloon 200 may be mainly expanded in a direction of increasing the diameter of the balloon 200 and increasing the area of a lateral surface. Because a female vaginal canal has a first side connected to a uterine neck, and a second side connected to the outside, the vaginal canal is not much changed in length but generally enlarged in a direction of increasing circumference. The vaginal canal has a lot of wrinkles in a contraction state, and the vaginal canal is unwrinkled and increased in circumference and diameter when the vaginal canal is enlarged. Thus, the balloon 200 is increased in diameter in the state of being inserted into the vaginal canal, and gradually unwrinkles the vagina inner-wall t to increase the area of contact with the outer surface of the balloon 200.

When the balloon 200 is contracted by releasing internal fluid pressure applied to the balloon 200, the shape of the balloon 200 is changed in a reverse way to that of when expanded. Further, the balloon 200 is contracted to some extent by the vaginal canal's own elasticity and body pressure. To maximize the contraction, negative pressure may be applied to the inside of the balloon 200.

The shaft 110 is partially inserted in the balloon 200 at the side of the grip unit 600, and the shaft 110 and the balloon 200 are attached at an insertion portion of the shaft 110 so as to seal up the inside and the outside of the balloon 200. Meanwhile, the operations of the balloon 200 will be additionally described later with reference to FIG. 6.

The energy transferer 301 is provided on an outer surface of the balloon 200 so as to be in contact with the inner surface of the vaginal canal, thereby transferring the RF energy. The energy transferer 301 may include a base 310, the electrodes 320 and the temperature sensor 330. The energy transferer 301 may be flexible and changed in shape as supported onto the balloon 200 at the expansion, and restored at the contraction. Further, the energy transferer 301 is flexible and thus transformed to some extent corresponding to the wrinkle or curvature C of the vagina inner-wall t when the balloon 200 expands to thereby enlarge the vaginal canal. In this regard, detailed descriptions will be made later with reference to FIGS. 7 and 8.

Although it is not shown, the insertion unit 100 may further include a sheath 400 surrounding the shaft 110 and the balloon 200 so as to be easily inserted into the vaginal canal. The sheath 400 may have a cross-section shaped like 'C' in order to be separated from the insertion unit 100 in the state of being inserted in the vaginal canal and taken outward, so that a user can pull and remove the sheath 400 at the outside.

Figure 5A:
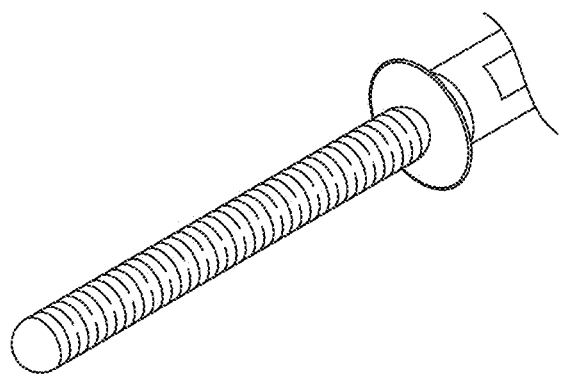
FIGS. 5a to 5c illustrate operations of the handpiece.
Figure 5B:
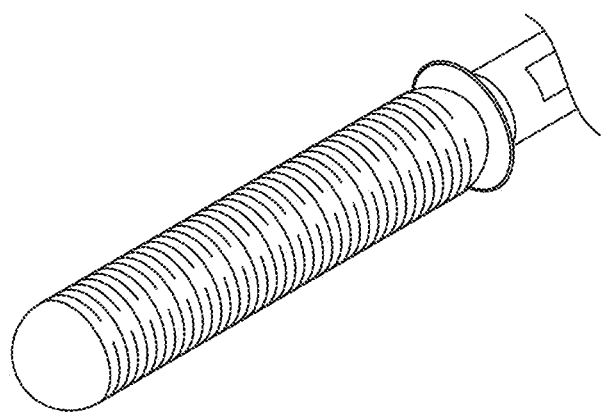
Figure 5C:
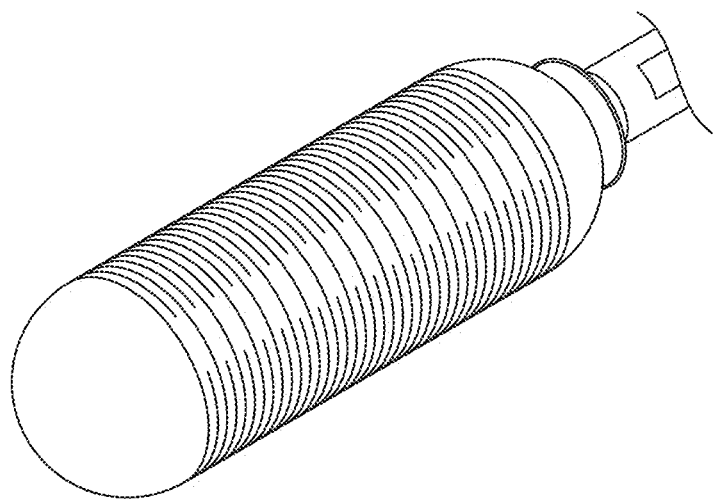

FIGS. 5a to 5c illustrate operations of the handpiece 10.

As shown in FIG. 5a, the insertion unit 100 of the handpiece 10 may be contacted as a first shape and expanded as a second shape. Here, the first shape refers to a state that the insertion unit 100 is pressed against the shaft 110 and fully compressed. The insertion unit 100 enters in a compressed or contracted state so as to be easily inserted into the vaginal canal. When the balloon 200 is expanded as shown in FIG. 5b, the insertion unit 100 is increased in diameter and the balloon 200 expands. The expansion of the insertion unit 100 causes the balloon 200 to expand so that the rolled-up energy transfer module transfer module can be gradually unrolled, and thus the outer surface of the insertion unit 100 can be continuously surrounded by the energy transfer module. Then, when the balloon 200 is furthermore expanded as shown in FIG. 5c, the insertion unit 100 has the maximum diameter, thereby maximizing a contact area formed on the circumferential outer surface. In this case, the insertion unit 100 includes a first expansion portion 210 having a cylindrical shape in the middle thereof, and a second expansion portion 220 having a hemispherical shape at an insertion-directional end thereof. Thus, main expansion occurs in a direction of increasing the diameter and the circumference.

Figure 6A:
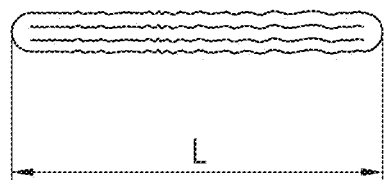
FIGS. 6a to 6c illustrate operations of a balloon.
Figure 6B:
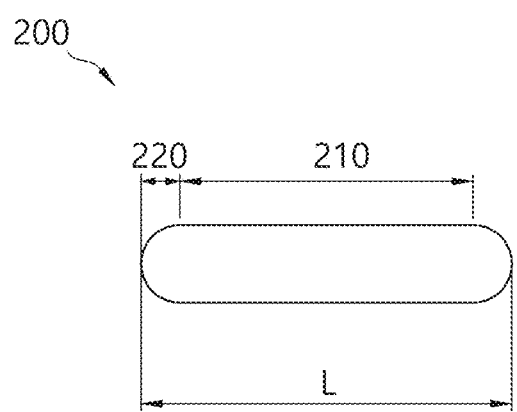
Figure 6C:
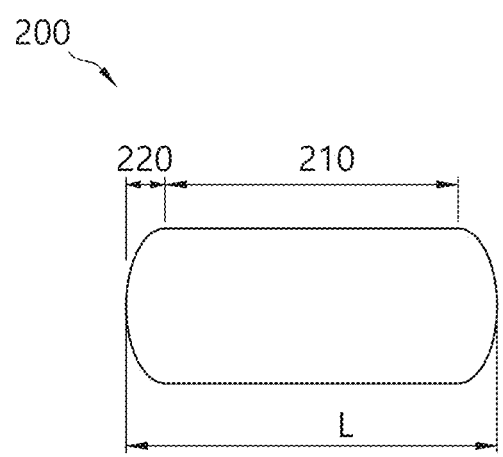

FIGS. 6a to 6c illustrate operations of the balloon 200.

FIG. 6a shows a contracted state of the balloon 200, FIG. 6b shows an intermediate expanded state of the balloon 200, and FIG. 6c shows a fully expanded state of the balloon 200.

As shown therein, the balloon 200 is configured to contract and expand, and configured to expand while maintaining a length L and also maintaining an overall shape when expanded. Here, the maintained length means that change in length is very small as compared with change in width even though the length is changed to some extent. The balloon 200 may be a semi-compliance balloon 200 which is a little wrinkled in the contraction state, and expands while keeping an overall shape after changed to have a certain shape. However, when the balloon 200 is a compliance balloon 200 which is continuously expanded from an initial state like a balloon and has a shape adjustable by external force, the compliance balloon 200 may expand maintaining a proper shape with the energy transferer 301 placed on the outer surface thereof. The balloon 200 may include latex, and may include various flexible materials suitable for a medical purpose.

Figure 7:
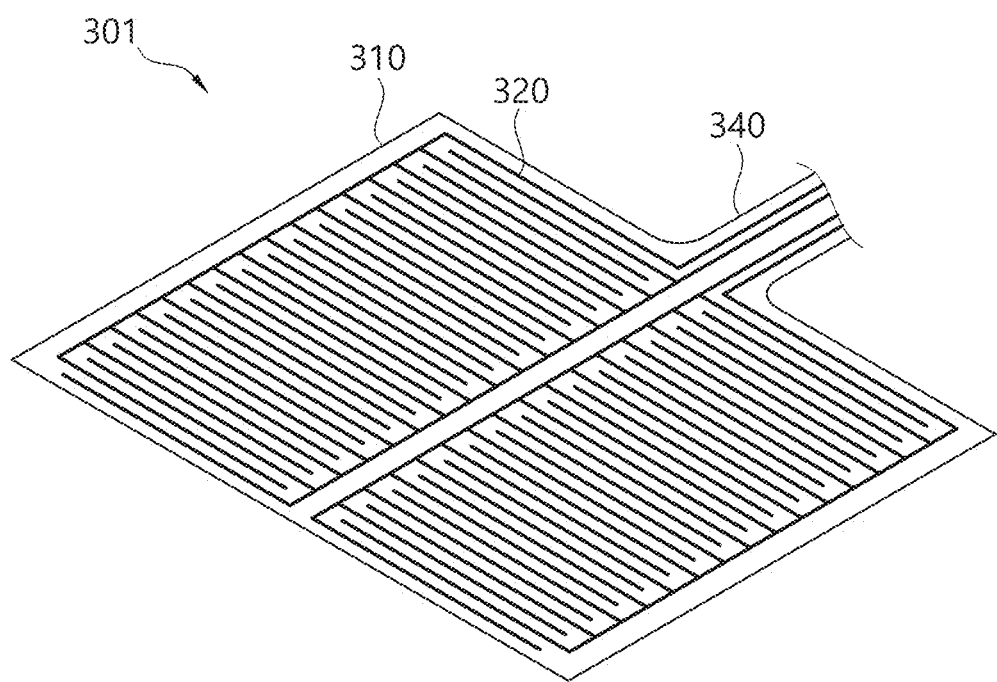
FIG. 7 is a planar view of an energy transfer module.
Figure 8:
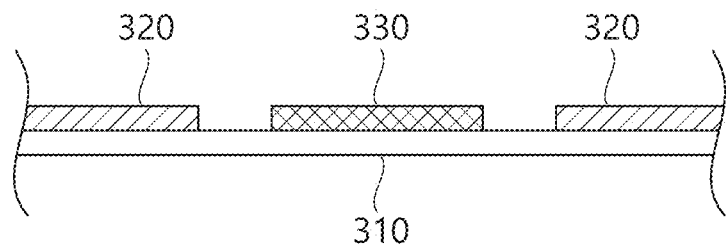
FIG. 8 is a cross-sectional view taken along I-I' of FIG. 7.

FIG. 7 is a planar view of an energy transferer 301, and FIG. 8 is a cross-sectional view taken along I-I' of FIG. 7.

As described above, the energy transferer 301 may include the base 310, the electrodes 320, the temperature sensor 330, and a connecting portion 340.

The base 310 has a space on which the electrodes 320 are placed, and the contact area of the electrodes 320 is varied depending on the expansion of the balloon 200. The base 310 is made of a flexible or elastic material, and configured to cope with the expansion of the balloon 200. The base 310 may for example be configured to rolled up in the circumferential direction of the balloon 200, and configured to gradually unroll and increase the area of the outer surface thereof as the balloon 200 expands.

The base 310 is configured to include the electrodes 320 on the outer surface thereof. The base 310 has an overall quadrangular shape when unrolled, and includes a plurality of electrodes 320 so that the electrodes 320 can be in contact with uterine lining at a plurality of points. When the base 310 is rolled up around the balloon 200, the electrodes 320 formed on the outer surface thereof are also rolled up, and thus varied in the area of contact with the uterine lining.

In this case, the base 310 may be configured to surround the lateral side of the balloon 200 except the end side of the balloon 200 in order to prevent energy from being transferred to a part of genitalia, in which contact occurs in a lengthwise direction, for example, the uterine neck and the like part.

The base 310 includes the connecting portion 340 at the first side thereof to electrically connect with the grip unit 600. The connecting portion 340 is relatively narrow as compared with the width of the base 310, and may include electric paths for individually controlling the plurality of electrodes 320 when the plurality of electrodes 320 are arrayed. The connecting portion 340 may be made of the same or similar elastic or flexible material as that of the base 310 for the purpose of flexible connection and damage prevention when the shape of the base 310 is changed as the balloon 200 expands. A portion where the connecting portion 340 and the base 310 are connected may be rounded to prevent stress from being focused thereon when the base 310 is changed in shape or the insertion unit 100 is pulled out from the vaginal canal. Although it is described by way of example that the connecting portion 340 is directly connected to the grip unit 600, the connecting portion 340 may be connected to the grip unit 600 through the shaft 110.

Meanwhile, the base 310 may include an attachment portion to be attached to the balloon 200. The attachment portion has a long region in a lengthwise direction so that a portion of which expansion is restricted by the attachment portion can be minimized when the balloon 200 is expanded in the circumferential direction, and a function of limiting lengthwise expansion can be additionally implemented. The attachment portion may be formed in a center portion of the electrodes 320 so that resistance generated by friction in an overlapped portion of the base 310 can be minimized when the balloon 200 expands. In other words, half of the base 310 with respect to the attachment portion surrounds the balloon 200 in a clockwise direction, and the other half surrounds the balloon 200 in a counterclockwise direction. Therefore, the base 310 is evenly unrolled in opposite directions corresponding to the expansion of the balloon 200, thereby remarkably reducing the friction as compared with that of when the base 310 is unrolled in only one direction, and eventually causing the expansion to be smoothly carried out.

The length of the base 310 may be determined to have an at least partially overlapped portion even when the balloon 200 expands up to the maximum size inside the vaginal canal. For removal from the vaginal canal after the treatment is finished, decrease in diameter is also required like that for the insertion, thereby preventing the vagina inner-wall t from being wounded and preventing a patient's suffering or discomfort. Therefore, when the base 310 has a partially overlapped portion even in the maximum expansion, the opposite sides of the base 310 support each other in the overlapped portion, so that the base 310 can return to be rolled up around the balloon 200. In this case, to smoothly return to the original rolled-up state, a flat spring or the like resilience provider (not shown) may be additionally provided. Alternatively, the base 310 may be provided to spirally surround the balloon 200, or may be provided to variously surround the balloon 200.

The electrodes 320 are configured to transfer energy through the uterine lining as described above. A plurality of electrodes 320 may be provided in an outward large surface of the base 310 when the base 310 surrounds the balloon 200. The electrodes 320 may be provided as a bipolar type and repetitively arrayed. The electrodes 320 may be arrayed in parallel along the circumferential direction so that the electrodes 320 can be pressed against the uterine lining while having uniform distribution density even at the expansion. The electrodes 320 may be connected to independent electric paths to be independently controlled according to a plurality of control regions divided on the plane of the base 310. The electrodes 320 are provided on the circumference of the balloon 200 along the base 310 and apply energy up to a predetermined depth of the uterine lining, thereby performing the treatment. Therefore, tissue treatment regions are formed in a rotating direction along the array of the electrodes 320, and an annular treatment region may be formed based on treatment of a predetermined depth. Although it is described that the electrodes 320 are the bipolar type, the electrodes 320 may be a monopolar type. In this case, a pad of the electrodes 320 may be separately provided to be in contact with the outside.

The electrodes 320 may be divided and arrayed in a plurality of regions along the circumference in order to prevent the RF energy from being transferred to an overlapped portion of the energy transferer 301, in other words, a portion not in contact with the tissue.

The temperature sensor 330 may be configured to sense a temperature of tissue. As the RF energy is transferred, the temperature of the tissue is changed. The temperature sensor 330 is configured to sense such a changed temperature and transmit a measured value to the controller 22. The temperature sensor 330 may be provided in plural to measure temperatures of the tissue at a plurality of points.

However, the temperature sensor 330 may be variously positioned, and thus descriptions thereof will be omitted. Further, the configuration may be variously applicable, and thus descriptions thereof will be omitted.

Although it is not shown, the energy transferer 301 may include insulation for the plurality of regions as necessary.

Below, use of the first embodiment according to the disclosure will be described in detail with reference to FIGS. 9 and 10. FIGS. 9a to 9c illustrate a using state according to the first embodiment, and FIGS. 10a to 10c illustrate expansion of the insertion unit 100 and enlargement of a lesion part. Meanwhile, expression may be a little exaggerated for convenience of description.

Figure 9A:
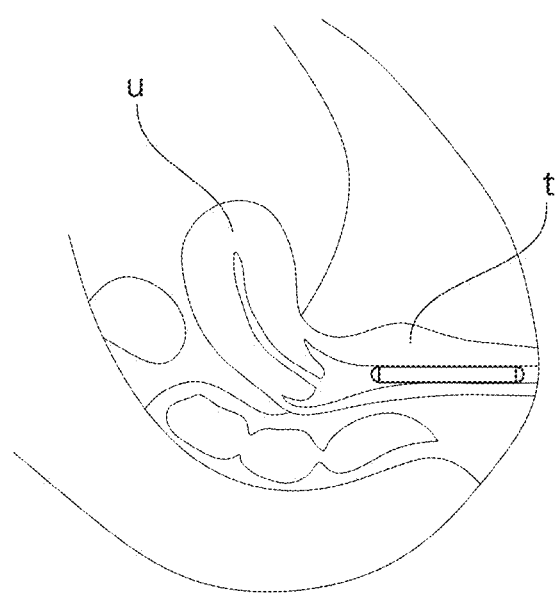
FIGS. 9a to 9c illustrate a using state according to the first embodiment.

As shown in FIG. 9a, insertion is carried out through a vaginal opening in a state that the insertion unit 100 is contracted. For smooth insertion, synovial fluid may be applied to the outer surface of the energy transferer 301. A user grips the grip unit 600 of the handpiece 10 and inserts the insertion unit 100 through the vaginal opening. In this case, the depth of the vaginal canal is different according to individuals, and thus the insertion depth of the insertion unit 100 may be different according to the individuals. The insertion unit 100 may be inserted up to a depth where the end of the insertion unit 100 is adjacent to or pressed against the uterine neck.

Figure 9B:
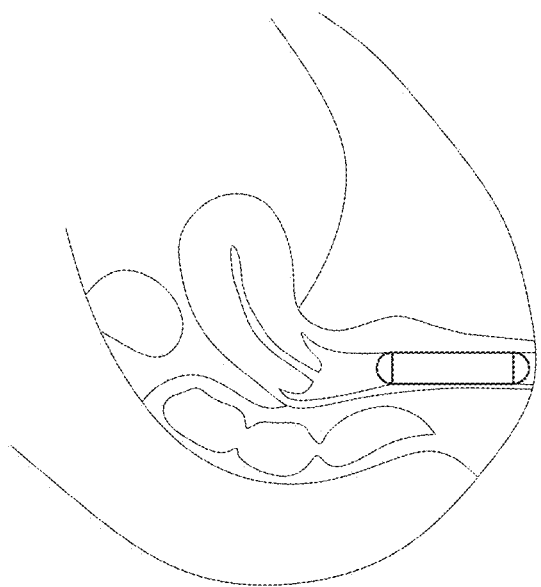

As shown in FIG. 9b, the insertion unit 100 expands after the insertion. In this case the controller 22 operates the fluid supplier 23 to supply the fluid to the balloon 200. In this case, the fluid is filled in the balloon 200 so that the balloon 200 can expand, thereby unrolling the electrodes 320 and enlarging the uterine lining. In this case, the expansion mainly occurs in the circumferential direction as the balloon 200 expands in the circumferential direction and the vagina inner-wall t also expands in the circumferential direction. In this case the controller 22 may supply the fluid by pressure higher than the body pressure. When the insertion unit 100 expands to enlarge the vagina inner-wall t, the balloon 200 expands only after the inner pressure of the balloon 200 becomes higher than the body pressure because of the body pressure and the elasticity of the vagina inner-wall t, the elasticity of the balloon 200, and the resilience of the energy transferer 301. After the expansion of the balloon 200, the amount of expansion is maintained by maintaining the pressure acting on the balloon 200.

Figure 9C:
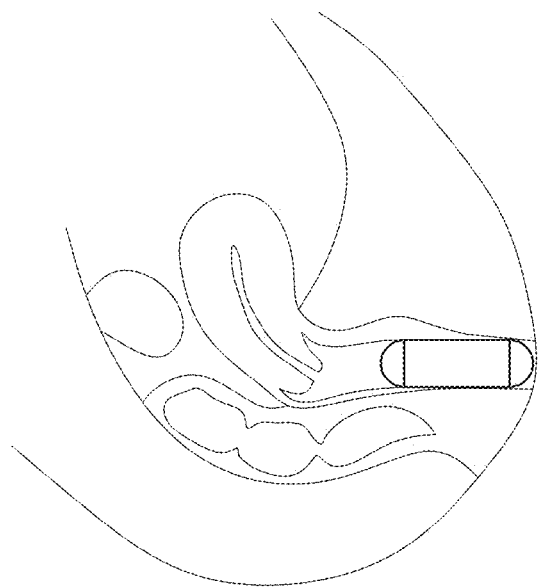

As shown in FIG. 9c, the controller 22 is configured to transfer the RF energy in the state that the balloon 200 is expanded. In this case, the energy transferer 301 is unrolled and becomes in contact with the vaginal canal lining through a large area, thereby transferring the RF energy. After transferring proper RF energy based on a preset treatment process, the balloon 200 is contracted and the insertion unit 100 is pulled out from the vaginal canal.

Figure 10A:
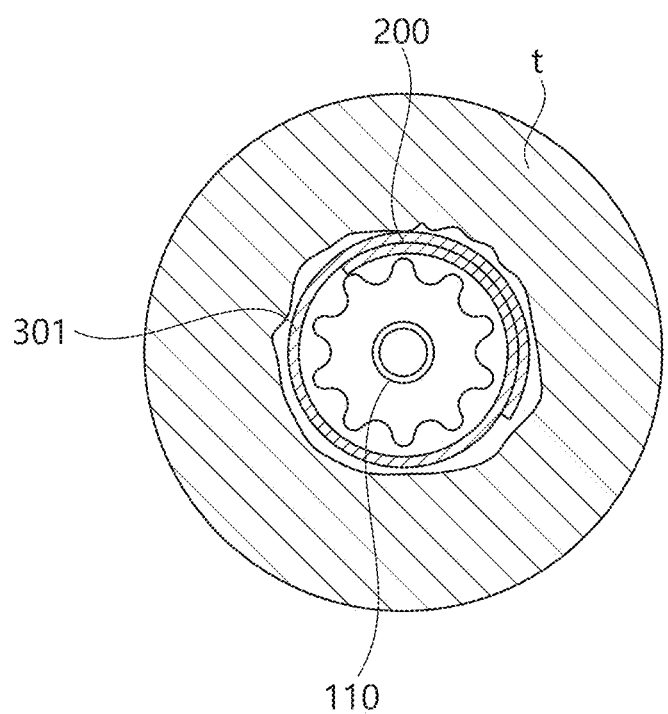
FIGS. 10a to 10c illustrate expansion of an insertion unit and enlargement of a lesion part.

Referring to FIG. 10, change in cross-section of the insertion unit 100 and the vaginal canal is illustrated corresponding to FIGS. 9a to 9c. As shown in FIG. 10a, in the insertion stage, the uterine lining is considerably wrinkled and therefore dispersely has portions not in contact with the outer surfaces of the electrodes 320.

Figure 10B:
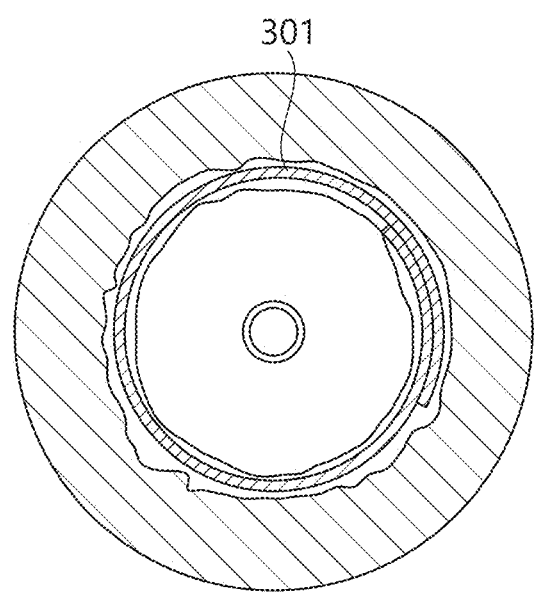

Referring to FIG. 10b, as the balloon 200 expands, the energy transferer 301 is unrolled and the vaginal canal is also enlarged. As the energy transferer 301 is unrolled, a contact area between the vagina inner-wall t and the electrodes 320 gradually increases.

Figure 10C:
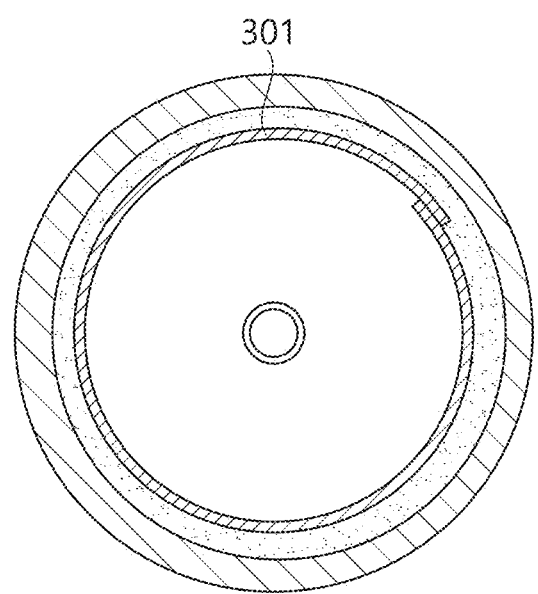

Referring to FIG. 10c, as the balloon 200 expands, the energy transferer 301 is unrolled and at the same time the vaginal canal is enlarged, thereby making most of the vagina inner-wall t be in contact with a module of the electrodes 320. Then, the RF energy is transferred while the expanded state is maintained. In this case, each pair of electrodes 301 locally transfers the energy and heats the tissue, and a treatment region may be annularly formed by one-shot treatment because a plurality of arrays is provided long the circumference of the energy transferer 301.

Below, alternative examples of the module of the electrodes 320 and the electrodes 320 will be described with reference to FIGS. 11 and 12.

Figure 11:
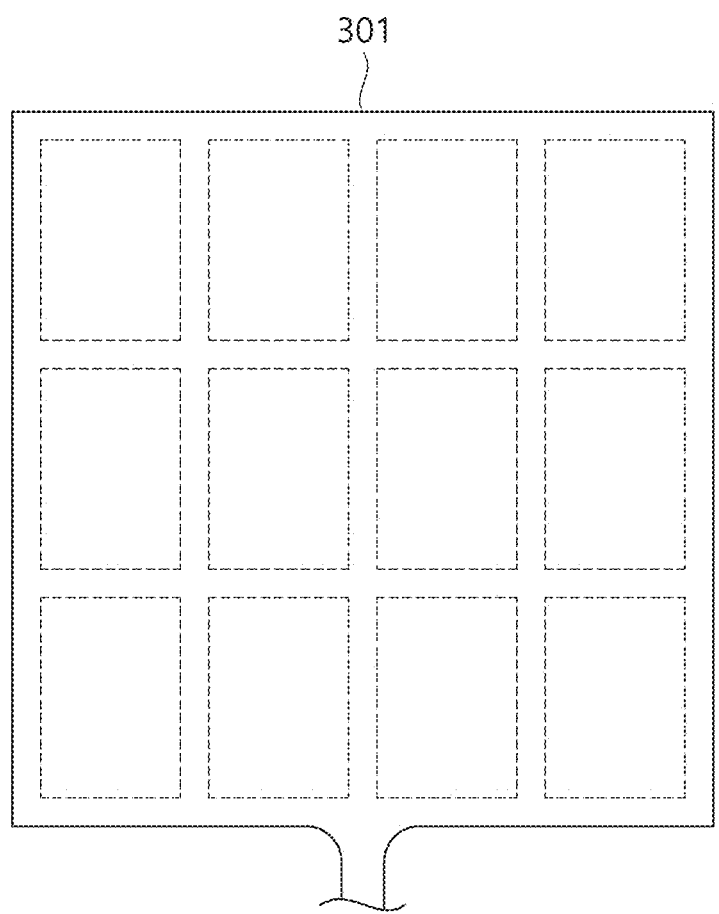
FIG. 11 is an alternative example of an electrode.

FIG. 11 is an alternative example of the energy transferer 301. As shown therein the energy transferer 301 may be arrayed in a plurality of rows and columns in a lengthwise direction and a circumferential direction. The plurality of electrodes 320 is configured to be independently controlled to transmit the RF energy according to unit regions (broken lines). With this array of the plurality of electrodes 320, it is possible to prevent the energy from being transferred from an uninserted portion of the insertion unit 100 according to regions when insertion depth is different according to individuals, and prevent the energy from being transferred to an overlapped portion of the energy transfer 301, in other words, the electrodes 320 not in contact with the tissue.

Figure 12:
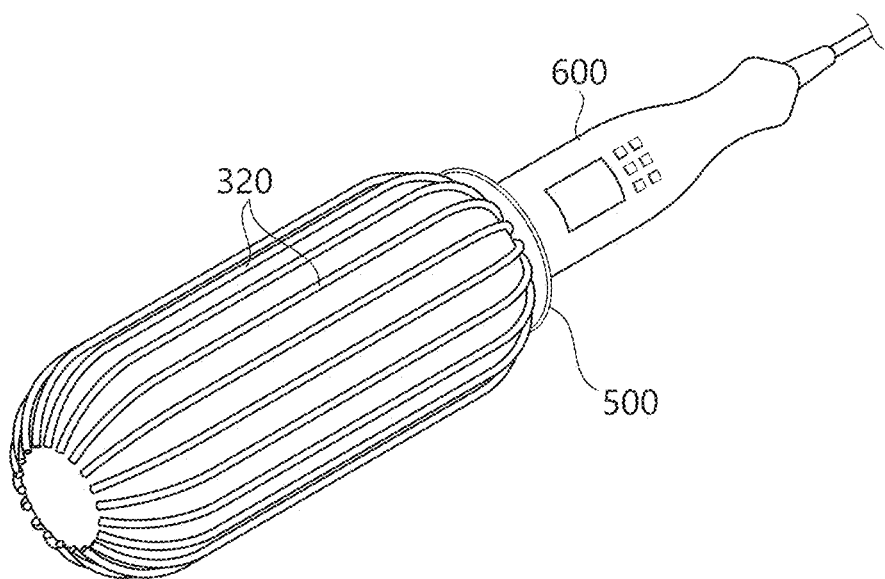
FIG. 12 is another alternative example of the electrode.

FIG. 12 is another alternative example of the electrodes 320. As shown therein, the electrodes 320 may be formed as printed on the outer surface of the balloon 200. In the state that the balloon 200 is being expanded, the electrodes 320 may be printed on the outer surface of the balloon 200, and pairs of electrodes 320 may be individually controlled. On the other hand, the electrodes 320 may be printed while the balloon 200 is being contracted, and stretched as the balloon 200 expands. The electrodes 320 may be formed by directly printing a conductive material on the outer surface of the balloon 200, or may be printed on a buffer provided on the outer surface of the balloon 200. Although it is illustrated that the electrodes 320 are printed on the balloon 200 in a lengthwise direction, this is merely an example and the electrodes 320 may be printed in a circumferential direction or formed as spots at a plurality of points.

Meanwhile, although it is not illustrated, the energy transferer 301 may be provided as a plurality of individual modules and attached to the outer surface of the balloon 200 leaving a predetermined angle therebetween. In this case, the shape may be smoothly changed corresponding to a curvature C of vaginal lining, and the distribution density of the electrodes 320 per unit area may be changed based on the expansion, thereby controlling the treatment region.

Below, a second embodiment according to the disclosure will be described in detail with reference to FIG. 13. The second embodiment may include the same elements as the first embodiment, and thus only different elements will be described to avoid repetitive descriptions.

Figure 13A:
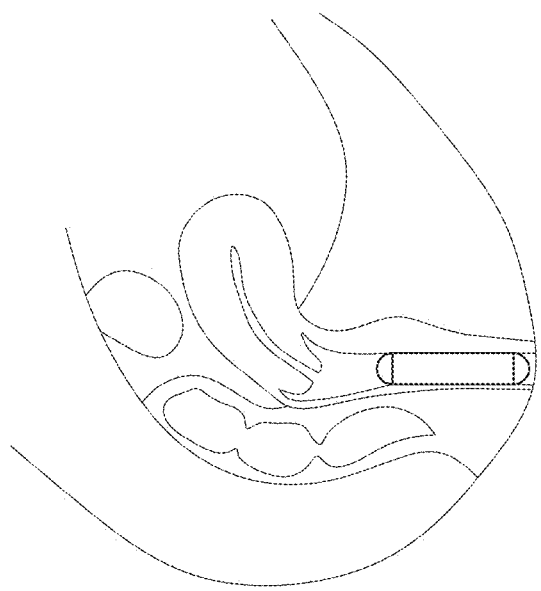
FIGS. 13a and 13b illustrate a using state according to a second embodiment.
Figure 13B:
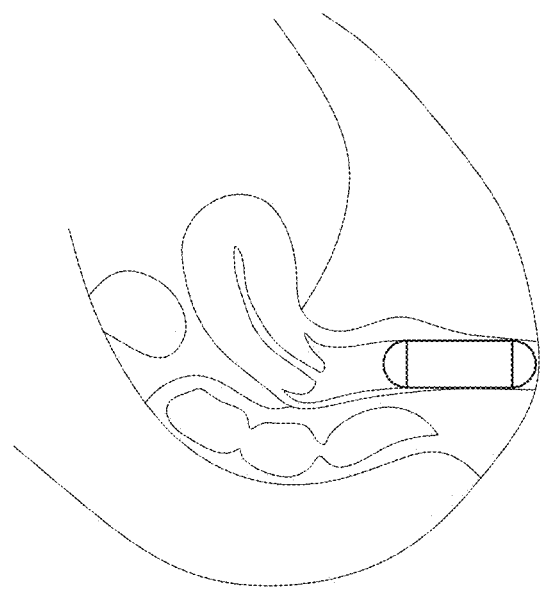

FIGS. 13a and 13b illustrate a using state according to a second embodiment. As shown therein, the insertion unit 100 of this embodiment in the contracted state is thicker than that of the first embodiment. In this case, the shaft 110 is thickly formed, and configured to further enlarge the vaginal canal when inserted in the vaginal canal. Next, the maximum expansion of the insertion unit 100 may be the same as that of the first embodiment (FIG. 13b)

In the case where the insertion unit 100 is relatively thick in the contracted state like this embodiment, the expansion of the vaginal canal may be achieved at the same time when the insertion unit 100 is inserted (FIG. 13a), and then the balloon 200 is expanded, thereby guaranteeing the minimum expansion amount of the vagina inner-wall t, and guaranteeing the minimum expansion shape because the expansion is made corresponding to the shape of the insertion unit 100.

Below, methods of controlling a vaginal-canal treatment device according to the disclosure will be described with reference to FIGS. 14 and 15.

Figure 14:
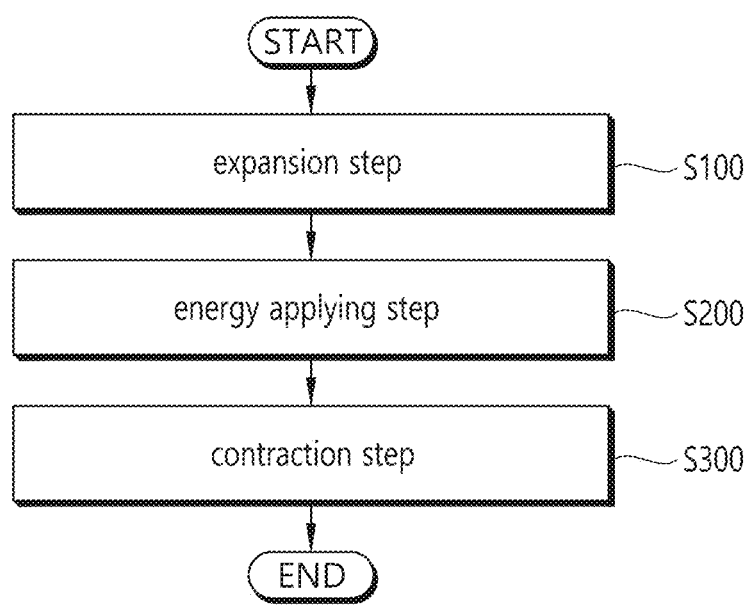
FIG. 14 is a flowchart showing a method of controlling a vaginal-canal treatment device according to another embodiment of the disclosure.

FIG. 14 is a flowchart showing a method of controlling a vaginal-canal treatment device according to an embodiment of the disclosure.

As shown therein, the method of controlling the vaginal-canal treatment device according to the disclosure may include an expansion step S100, an energy applying step S200, and a contraction step S300.

The expansion step S100 refers to a step of expanding the treatment device inserted in the vaginal canal within a predetermined range. When the treatment device inserted in the vaginal canal is expanded, a contact area between a wrinkled vagina inner-wall t and the treatment device increases. In this case the expansion of the treatment device may expand the expansion portion provided in the treatment device. When a user makes a start input, the treatment device gradually expands the expansion portion up to a predetermined range. In this case an expanded amount may be carried out within a preset range, and controllable based on a user's input.

The energy applying step S200 refers to a step of supplying energy to energy transfer elements provided in the expansion portion. In this case the contact area between the expansion portion and the vagina inner-wall t, and the insertion depth may be sensed to adjust the energy to be transferred. When the energy is transferred, the temperature of tissue to which the energy is transferred is measured, thereby performing the feedback control. The tissue to which the energy is transferred is heated and denatured, thereby undergoing the treatment. Here, the energy may for example include various types of energy such as RF energy, a laser, light, an ultrasonic wave, etc.

The contraction step S300 refers to a step of contracting the expansion portion as a step before pulling out the expansion portion from the vaginal canal after applying the energy to the tissue. The expansion portion may be contracted into the minimum size to be easily removed from the vaginal canal.

Figure 15:
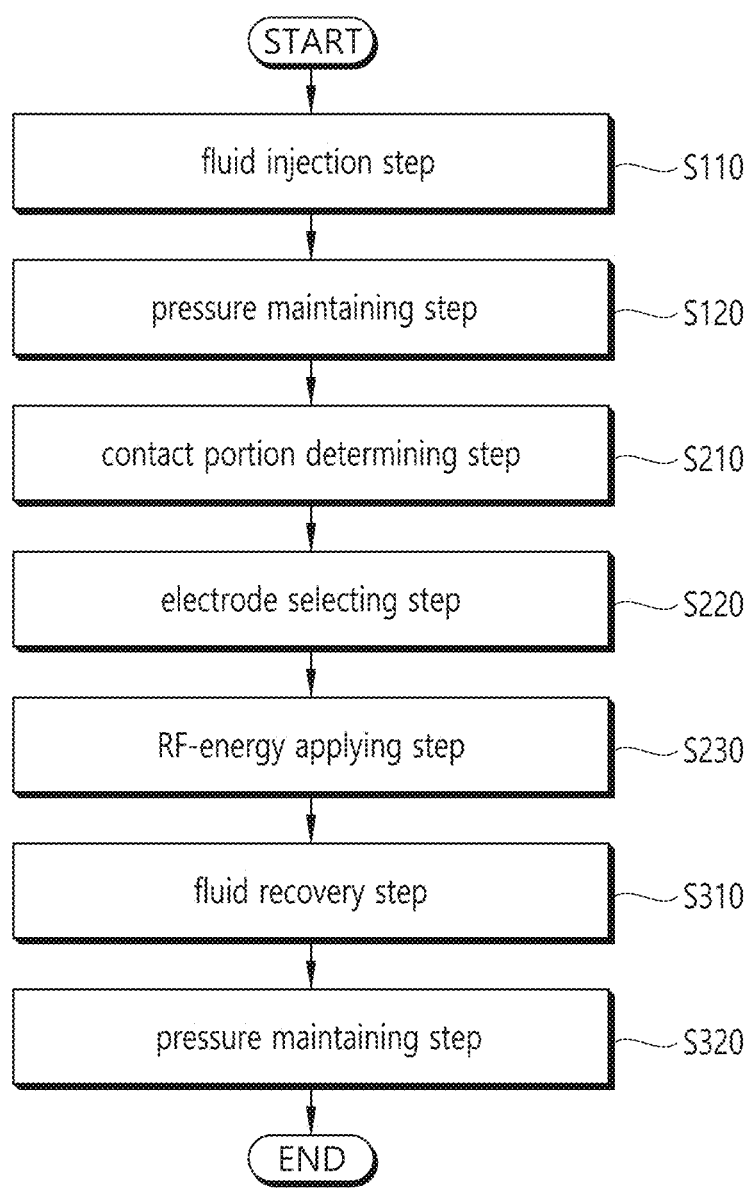
FIG. 15 is a flowchart showing a method of controlling a vaginal-canal treatment device according to another embodiment of the disclosure.

FIG. 15 is a flowchart showing a method of controlling a vaginal-canal treatment device according to another embodiment of the disclosure.

In this embodiment, the expansion step S100 may include a fluid injection step S110 and a pressure maintaining step S120. The energy applying step S200 may include a contact portion determining step S210, an electrode selecting step S220, and an RF-energy applying step S230. Further, the contraction step S300 may include a fluid recovery step S310 and a pressure maintaining step S320.

The fluid injection step S110 refers to a step of injecting fluid into the balloon inserted in the vaginal canal so that the balloon provided in the expansion portion can be expanded. When the fluid is injected, flow rate and flow pressure may be selectively controlled based on an expansion amount. The fluid injection may be performed by controlling the flow rate of the fluid supplied from the fluid supplier.

The pressure maintaining step S120 refers to a step of maintaining the expansion amount so that the contacted vagina inner-wall t can be fixed when the balloon is expanded within a proper range. In this case, configuration is achieved to maintain the pressure, and the pressure may be maintained by closing a fluid line connected to the balloon. Further, servocontrol may be used to provide uniform pressure.

The contact portion determining step S210 refers to a step of determining an electrode, which is in contact with vaginal lining, among electrodes provided in the expansion portion. Because the internal structure and size of the vaginal canal are different according to individuals, the contact portion may be varied when the expansion portion is expanded. It is possible to determine the contact portion and a non-contact portion which are different according to individuals.

The electrode selecting step S220 refers to a step of selecting non-contact electrodes to be excluded from energy-applying target electrodes so that the energy can be prevented from being applied to the selected electrodes when the energy is applied.

The RF-energy applying step S230 refers to a step of transferring the energy to the tissue by applying the RF energy through the selected contact electrodes. As the RF energy is transferred, the inner portion of the vaginal canal may be treated. In the RF-energy applying step S230, control may be achieved based on a preset program by mirroring personal electric properties of tissue.

The fluid recovery step S310 refers to a step of recovering the fluid so that the balloon can be contracted after the RF energy is completely applied. To recover the fluid, the fluid supplier 23 may generate negative pressure to discharge the fluid from the inside of the balloon to the outside. In this case, the balloon may be contracted by the vaginal canal's own pressure.

The pressure maintaining step S320 refers to a step of generating and maintaining negative pressure in the balloon so as to prevent the balloon contracted by the balloon's own elasticity from expanding a little. A user can remove the expansion portion from the vaginal canal in the state that the balloon is contracted as the negative pressure is maintained.

Although the negative pressure is described by way of example in the fluid recovery step S310 and the pressure maintaining step S320, pressure of various ranges may be used as long as which the balloon can be contracted inside the vaginal canal.

Figure 16:
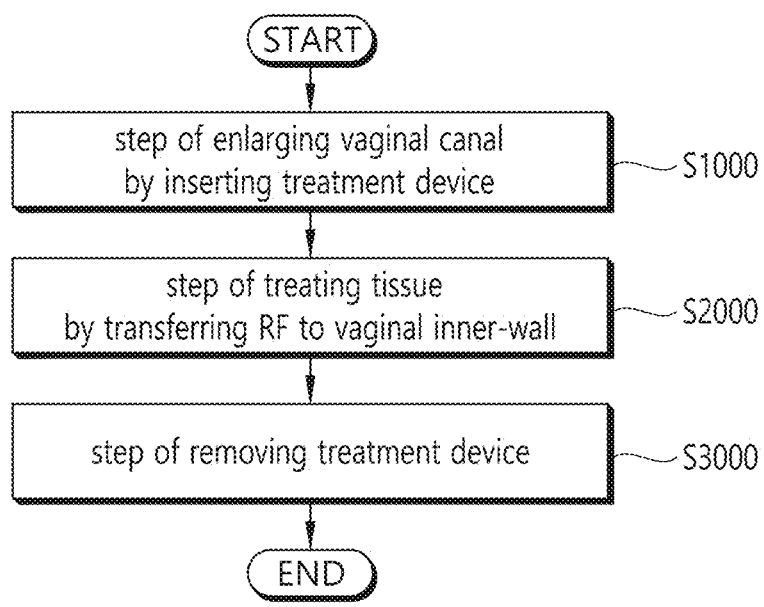
FIG. 16 is a flowchart showing a vaginal-canal treatment method according to another embodiment of the disclosure.

FIG. 16 is a flowchart showing a vaginal-canal treatment method according to another embodiment of the disclosure. As shown therein, the vaginal-canal treatment method includes a step S1000 of enlarging the vaginal canal by inserting the treatment device in the vaginal canal, a tissue treatment step S2000, and a step S3000 of removing the treatment device.

The step S1000 of enlarging the vaginal canal by inserting the treatment device in the vaginal canal refers to a step of enlarging the vaginal canal within a predetermined range by inserting the treatment device having a predetermined thickness into the vaginal carnal from entrance at a side of a pudendum. The treatment device to be inserted has a uniform thickness, thereby securing the enlargement of the vaginal canal.

The tissue treatment step S2000 refers to a step of treating the tissue by transferring energy toward the vagina inner-wall tin the state that the vaginal canal is enlarged. In the treatment of the tissue, the energy is transferred to heat and denature the tissue, so that the tissue can be remodeled through a predetermined convalescence.

The step S3000 of removing the treatment device refers to a step of pulling the treatment device out of the vaginal canal. For smooth removal and to prevent the vagina inner-wall from being wounded, the treatment device is contracted and then removed. Although it is not illustrated, the treatment device may be surrounded by the sheath 400 and then removed.

Figure 17:
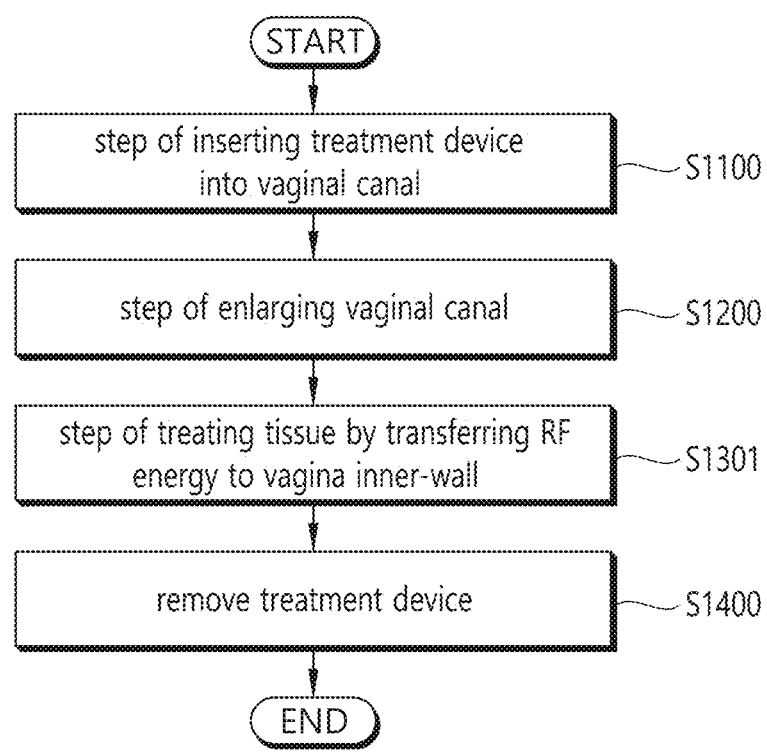
FIG. 17 is a flowchart showing a vaginal-canal treatment method according to another embodiment of the disclosure.

FIG. 17 is a flowchart showing a vaginal-canal treatment method according to another embodiment of the disclosure.

This embodiment may employ the same configuration as the foregoing treatment method, and, in this regard, only different configuration will be described avoiding repetitive descriptions. In this embodiment, the treatment is carried out by enlarging the vaginal carnal after the treatment device is inserted into the vaginal canal.

A step S1100 of inserting the treatment device into the vaginal canal refers to a step of inserting the treatment device through the vaginal opening from the pudendum of the female genitalia. In this case, the treatment device may be inserted as contracted to have the minimum diameter. When the treatment device is inserted, the position of the energy transferer 301 may be adjusted for the treatment of the vagina inner-wall. Further, although it is not illustrated, the sheath 400 surrounding the treatment device may be used for positioning and then the insertion may be completed by removing only the sheath 400.

A step S1200 of enlarging the vaginal canal refers to a step of expanding the expansion portion of the inserted treatment device to enlarge the vaginal canal. The enlargement of the vaginal canal is mainly carried out in the circumferential direction, and a contact area between an energy transfer module of the treatment device and the vagina inner-wall is increased as the vaginal canal is enlarged. In this case, an overall shape of the expansion may be a cylindrical shape. In this case, the treatment region may be a lateral side of the vaginal carnal expanded in the cylindrical shape.

Below, an energy transfer module for vaginal-canal treatment, a control method thereof, and a vaginal-canal treatment method using the same will be described in detail with reference to FIGS. 18 to 24.

Figure 18:
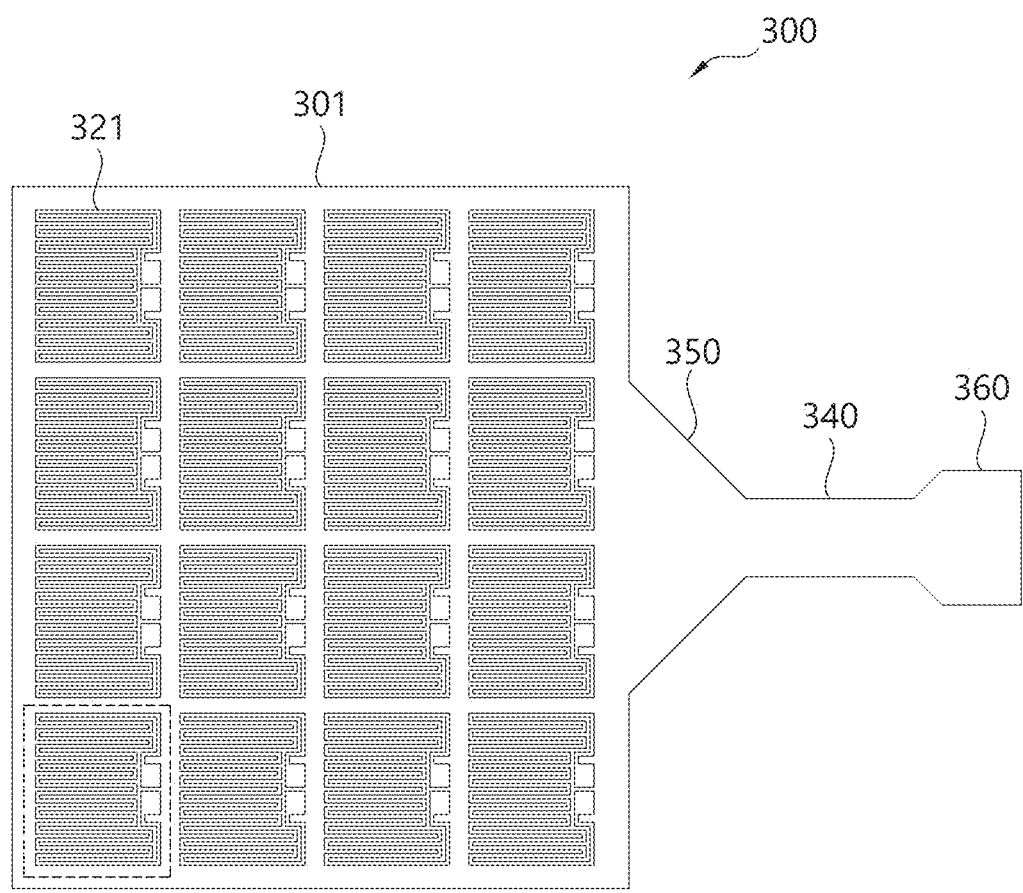
FIG. 18 is a plan view of an energy transfer module for a vaginal-canal treatment device according to another embodiment of the disclosure.
Figure 19:
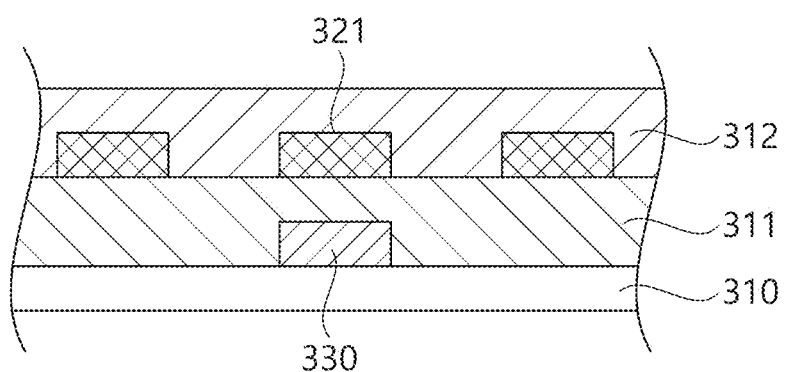
FIG. 19 is a partial cross-section view showing a partially cut-open portion of FIG. 18.

FIG. 18 is a plan view of an energy transfer module 300 for a vaginal-canal treatment device according to another embodiment of the disclosure, and FIG. 19 is a partial cross-section view showing a partially cut-open portion of FIG. 18.

As shown therein, the energy transfer module 300 for the vaginal canal treatment according to the disclosure includes a flexible substrate and a plurality of heating electrodes 321 provided on the substrate and configured to heat a treatment region.

The energy transfer module 300 is placed on an outer surface of the expansion portion and configured to heat a vagina inner-wall. The energy transfer module 300 may include an energy transferer 301 to be inserted into the vaginal canal, a connector 360 configured to be electrically connected to the outside, and an extended portion 340 configured to connect the energy transferer 301 and the connector 360.

The insertion unit is generally shaped like a quadrangular plate, and includes a first side configured as a support surface for contacting and supporting the foregoing expansion portion, and a second side configured to contact an external vagina inner-wall. The energy transferer 301 is inserted together with the expansion portion 200 into the vaginal canal in a state of being rolled as a cylindrical shape, and unrolled as supported by the expansion of the expansion portion 200. Further, when the expansion portion is contracted, the energy transferer 301 may be contracted by the vagina inner-wall's own resilience. The energy transferer 301 may be generally made of an elastic and transformable material.

The energy transferer 301 may include a base 310, a first layer 311, a second layer 312, a heating electrodes 321, a temperature sensor 330, an extended portion 340, an enlarged portion 350 and a connector 360.

The base 310 is made of an insulating material, and an elastic material, and used as a base on which other elements are arranged.

The first layer 311 is configured to electrically insulate heating electrodes 321 and a temperature sensor 330 (to be described later).

The second layer 312 is configured to insulate the heating electrodes 321 from the outside. The second layer 312 functions as an outermost layer in the energy transfer module 300, and is in direct contact with the vagina inner-wall when inserted into the vaginal canal. The second layer 312 may be made of an electrically insulating material. Further, the second layer 312 may be made of a material having high thermal conductivity to enhance an efficiency of receiving thermal energy from the heating electrodes 321 (to be described later) and transferring the thermal energy to the external vagina inner-wall.

The heating electrodes 321 are configured to receive electric energy and generate heat. The heating electrodes 321 may include surface heating electrodes 321 so as to heat a large area. A plurality of heating electrodes 321 are provided to independently heat individual regions defined by dividing the plane region of the flexible substrate into a plurality of regions. For example, as shown in FIG. 1, the individual regions may include 4×4 divisional regions. However, the individual region is merely an example, and may include various numbers of divisional regions.

The heating electrodes 321 is formed to have a shape extended in a predetermined width, and may be arranged zigzag in one individual region. Therefore, the electrodes are arranged in parallel with each other inside one individual region, and electric currents of most adjacent electrodes may flow in opposite directions. Therefore, when the electric current is applied, inductive heating occurs so that each electrode can generate heat. In this case, the electric current may employ an alternating current (AC) or a pulse wave current to generate heat. The heating electrodes 321 are formed on the first layer 311, and insulated from the outside by the second layer 312. Therefore, the heating electrodes 321 are not in direct-contact with the outside, i.e., the vagina inner-wall, and the generated thermal energy is transferred to the vagina inner-wall through the second layer 312. The heating electrodes 321 may be formed to have a proper thickness to be smoothly transformed when the substrate is transformed by the expansion of the expansion portion.

The temperature sensor 330 is configured to measure the temperature of the energy transfer module 300 or the vagina inner-wall as the temperature of the heating electrodes 321 is raised. The temperature sensors 330 may be respectively provided in the plurality of individual regions, or a plurality of temperature sensors 330 may be provided in each individual region. The temperature sensor 330 may be interposed between the base 310 and the first layer 311 as distinguished from the layer on which the heating electrodes 321 are arranged.

However, such arrangement of the temperature sensor 330 is merely an example, and the temperature sensor 330 may be provided at various positions as long as it can sense the temperature without affecting the electrodes. For example, the temperature sensor 330 may be provided together with the heating electrodes 321 between the first layer 311 and the base 310. In this case, the second layer 312 may be omitted based on the arrangement of the temperature sensor 330. Further, the temperature sensor 330 may be exposed to the outside and be in direct contact with the external vagina inner-wall.

Meanwhile, although it is not shown, a plurality of electric paths may be formed to be connected to each of the heating electrodes 321 and the temperature sensor 330.

The connector 360 is configured to be electrically connected to the handpiece. The connector 360 may be configured not to be substantially inserted into the vaginal canal.

The extended portion 340 is configured to connect the energy transferer 301 and the connector. The extended portion 340 is formed as extended from the first side of the energy transferer 301, and may be extended from the base 310, the first layer 311 and the second layer 312 of the energy transferer 301. The extended portion 340 is formed with the electric path extended from the energy transferer 301, and connected by the connector. The extended portion 340 may be narrower than the energy transferer 301 so as to be hardly changed even though the expansion portion is expanded. The extended portion 340 may not be substantially inserted in the vaginal canal.

The enlarged portion 350 may be formed and enlarged in a widthwise direction in a connecting portion between the energy transferer 301 and the extended portion 340, to which stress is focused. The enlarged portion 350 is configured to disperse the stress in a boundary portion where the energy transferer 301 is transformed and the transformation and stress are focused when the expansion portion is expanded. The enlarged portion 350 may be formed by enlarging the base 310, the first layer 311 and the second layer 312, and gradually become wider from the extended portion 340 toward the energy transferer 301.

Figure 20:
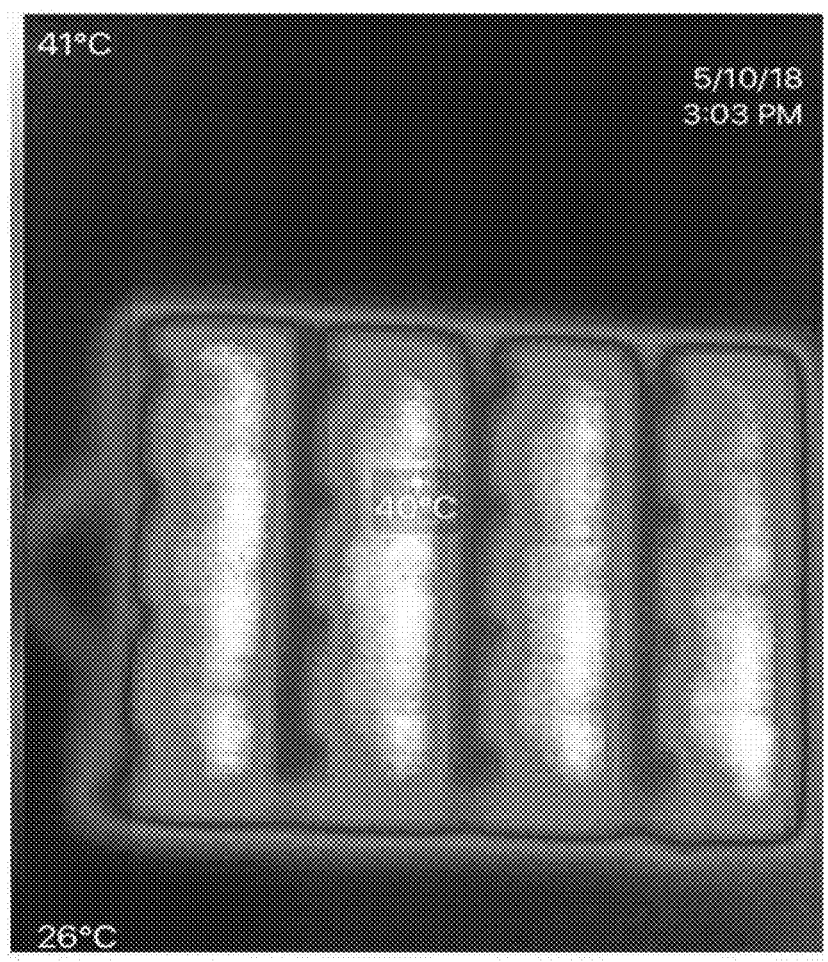
FIG. 20 is a thermal image showing a heating pattern when power is applied in FIG. 18.

FIG. 20 is a thermal image showing a heating pattern when power is applied in FIG. 18. As shown therein, when power is applied to the heating electrodes 321, the heating electrodes 321 are configured to autonomously generate heat even though there is no contact with external medium. Meanwhile, as shown therein, the heat generation may be focused by distinguishing between divisional regions, and although it is not shown, each region may individually generate heat based on power control of the controller.

Below, methods of controlling the energy transfer module 300 for the vaginal canal treatment, which includes the heating elements 321, will be described in detail with reference to FIGS. 21 and 22.

Figure 21:
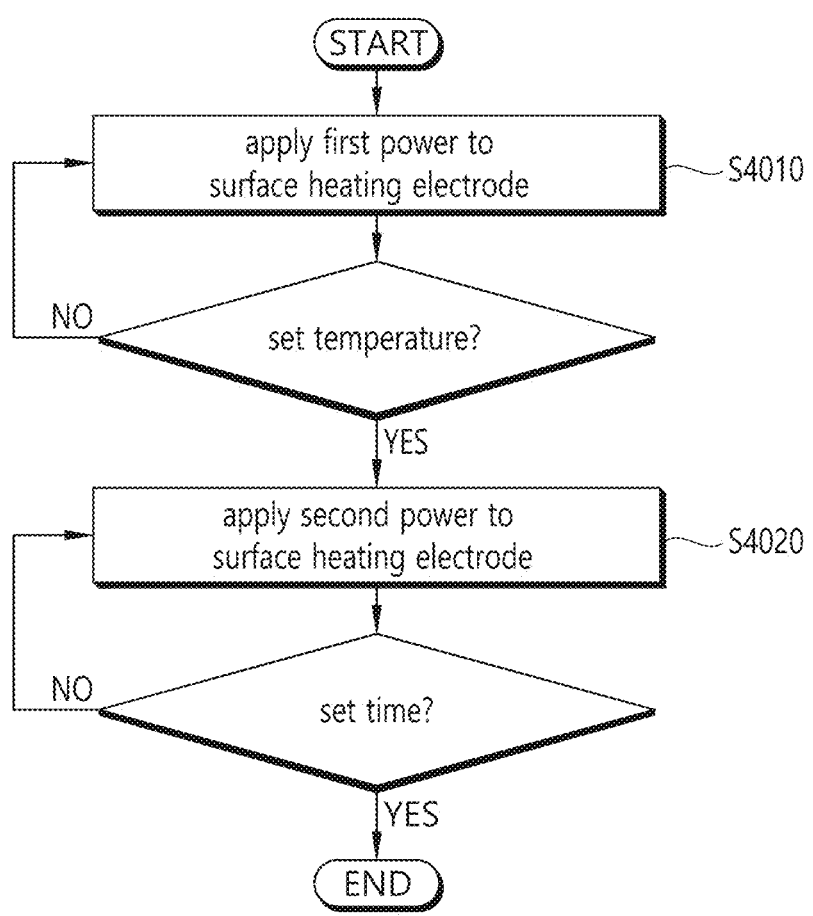
FIG. 21 is a flowchart showing a method of controlling an energy transfer module for vaginal canal treatment according to another embodiment of the disclosure.

FIG. 21 is a flowchart showing a method of controlling an energy transfer module for vaginal canal treatment according to another embodiment of the disclosure.

As shown therein, the method of controlling the energy transfer module with the heating electrodes for the vaginal canal treatment includes a step S4010 of applying first power to the surface heating electrode, and a step S4020 of applying second power to maintain the vagina inner-wall at a set temperature during a set time.

The step S4010 of applying the first power to the surface heating electrode refers to a step of applying AC to the heating electrodes 321 so that the energy transfer module 300 shown in FIG. 18 can be heated. As described above, when AC is applied to the heating electrodes 321, heat is generated without any separate external medium. In this step, a temperature measurement value measured by the temperature sensor 330 is fed back in order to raise temperature up to the set temperature. Meanwhile, as described above, the temperature sensor 330 senses the temperature of the energy transferer 301 or the temperature of the vagina inner-wall based on its installed positions, and therefore the set temperature may be varied depending on the installed positions. Here, the temperature for the vagina inner-wall may be set to 60° C., or the temperature for the energy transferer 301 may be set to 60° C.

In the step S4020 of applying the second power to maintain the vagina inner-wall at a set temperature during a set time, the second power may be determined to make the temperature of the vagina inner-wall be not higher than 60° C. but kept at 40° C. to 60° C. In this step, the set time may range several seconds to several minutes. Therefore, coagulation denaturation may occur in a contact part between the vagina inner-wall and the energy transferer 301.

Figure 22:
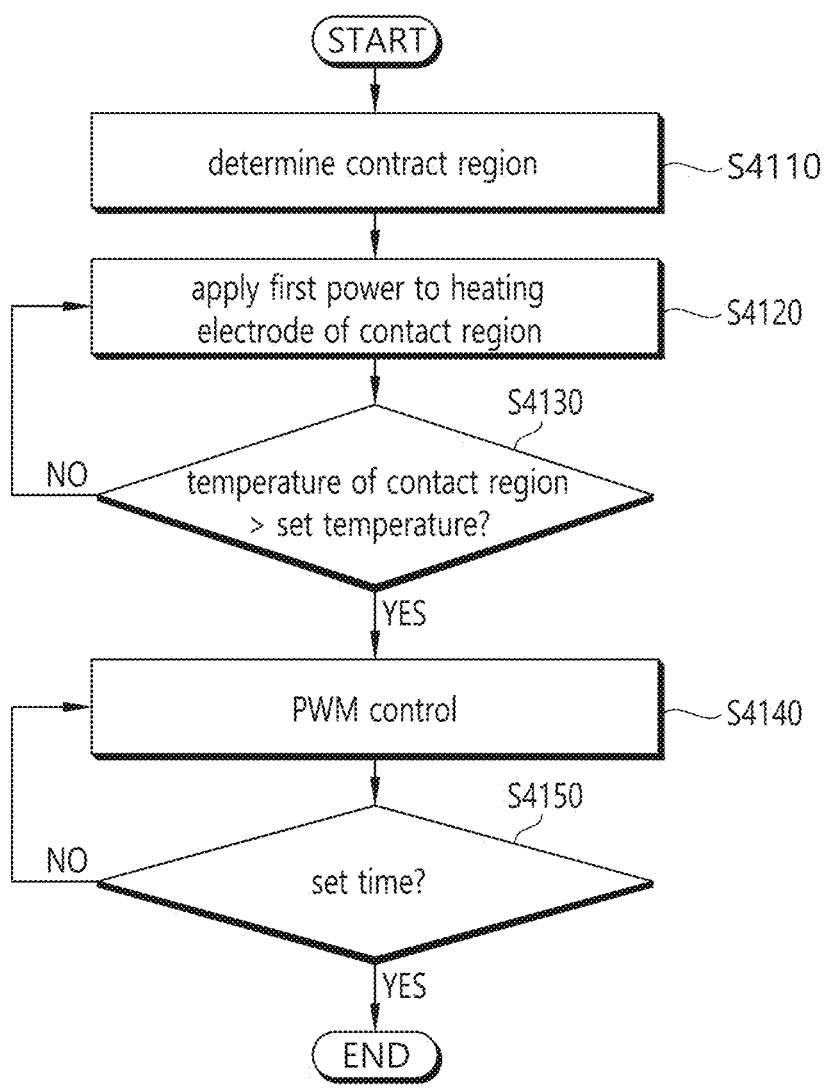
FIG. 22 is another flowchart showing a method of controlling an energy transfer module for vaginal canal treatment according to another embodiment of the disclosure.

FIG. 22 is another flowchart showing a method of controlling an energy transfer module for vaginal canal treatment according to another embodiment of the disclosure.

As shown therein, this control method is to individually heat a plurality of divisional regions. For example, when the energy transferer 301 of FIG. 18 is not fully unrolled but overlapped in a partial region or has a portion not inserted in the vaginal canal, a region being in contact with the vagina inner-wall is selectively heated except the overlapped region or sticking-out portion.

This control method may include a contact region determining step S4110, a step S4120 of applying first power to a heating electrode of a contact region, a step S4130 of determining the temperature of the contact region, a pulse width modulation (PWM) control step S4140, and a set-time lapse determining step S4150.

The contact region determining step S4110 is to determine contact with the vagina inner-wall when the expansion portion is expanded and the energy transferer 301 is unrolled. In the contact region determining step S4110, the region of contact with the vagina inner-wall of when the energy transferer 301 is inserted in the vaginal canal is checked out based on temperature measurement values measured at a plurality of points. The contact regions may be given in units of individual regions independently controllable by the heating electrodes 321.

The region of contact with the inner wall of the vaginal canal in the state that the energy transferer 301 is unrolled is raised in temperature from room temperature to body temperature at a similar rate. On the other hand, a region partially overlapped as the energy transferer 301 is not unrolled is not in direct contact with the inner wall of the vaginal canal and thus relatively slowly raised in temperature, thereby causing difference between the temperature measurement values. Further, a portion not inserted in a lengthwise direction is maintained at room temperature, and it is thus possible to determine the contact.

The step S4120 of applying the first power to the heating electrode of the contact region is to supply power to an individual region determined as the foregoing contact region. For example, AC power is applied so that the heating electrodes 321 can generate heat.

The step S4130 of determining the temperature of the contact region refers to a step of continuously measuring the temperature of the contact region and determining whether the measured temperature is raised up to the set temperature. For example, the set temperature may be 60° C.

The PWM control step S4140 refers to a step of controlling power so that the set temperature is maintained for a predetermined period of time after heating is carried out up to the set temperature. Because PWM control is applied to the heating electrodes 321 arranged in the individual contact regions, it is possible to control the heating amount. To control the heating amount, the PWM control is used by way of example, but voltage control may be used.

The set-time lapse determining step S4150 is to determine whether a treatment temperature is maintained for a predetermined period of time so that desired treatment can be performed. Here, the foregoing PWM control may be performed until the set time elapses.

Below, a vaginal-canal treatment method using the heating electrodes shown in FIG. 18 will be described with reference to FIGS. 23 and 24.

Figure 23:
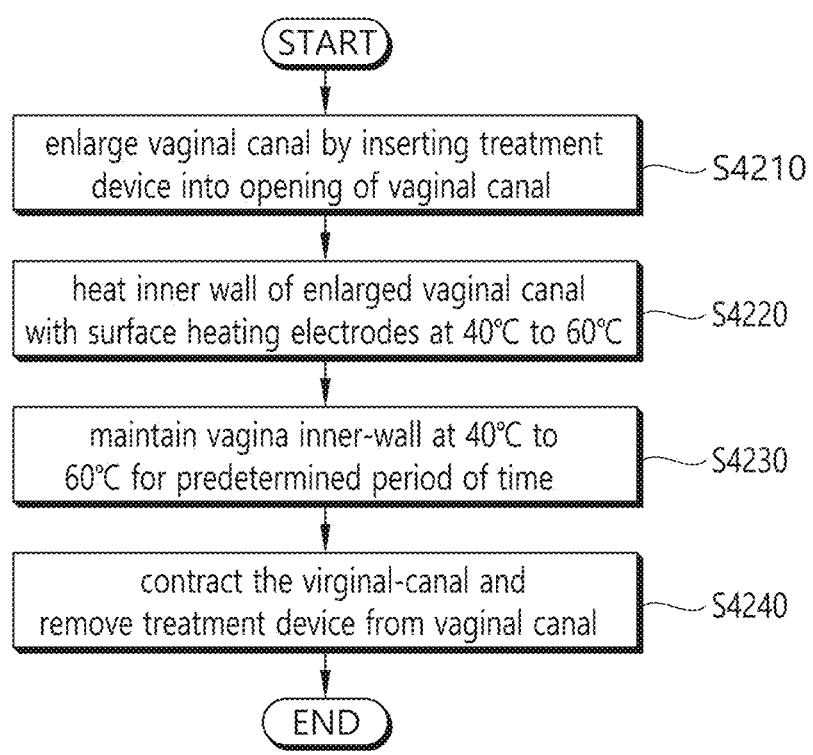
FIG. 23 is a flowchart showing a vaginal-canal treatment method using an energy transfer module for vaginal canal treatment according to another embodiment of the disclosure.

FIG. 23 is a flowchart showing a vaginal-canal treatment method using an energy transfer module 300 for vaginal canal treatment according to another embodiment of the disclosure.

As shown therein, this embodiment includes a vaginal-canal enlarging step S4210, a vaginal-canal heating step S4220, a step S4230 of maintaining the vagina inner-wall for a predetermined period of time, and a step S4240 of contracting the vaginal-canal and removing the treatment device from the vaginal canal.

The vaginal-canal enlarging step S4210 refers to a step of inserting the insertion unit of the treatment device provided with the heating electrodes 321 shown in FIG. 18 into the opening of the vaginal canal, expanding the expansion portion, and enlarging the vagina inner-wall. Here, the expansion of the expansion portion may be performed by injecting the fluid through a manual or automatic pump as described above.

The vaginal-canal heating step S4220 refers to a step of heating the lateral surface of the enlarged vaginal canal by the surface heating electrodes 321. The vagina inner-wall is heated at 40° C. to 60° C.

The step S4230 of maintaining the vagina inner-wall for a predetermined period of time refers to a step of maintaining the vagina inner-wall at 40° C. to 60° C. for a predetermined period of time so as to achieve the treatment. The vagina inner-wall is maintained at 40° C. to 60° C. for a predetermined period of time so that the tissue can be denatured by heating to produce coagulation.

Figure 24:
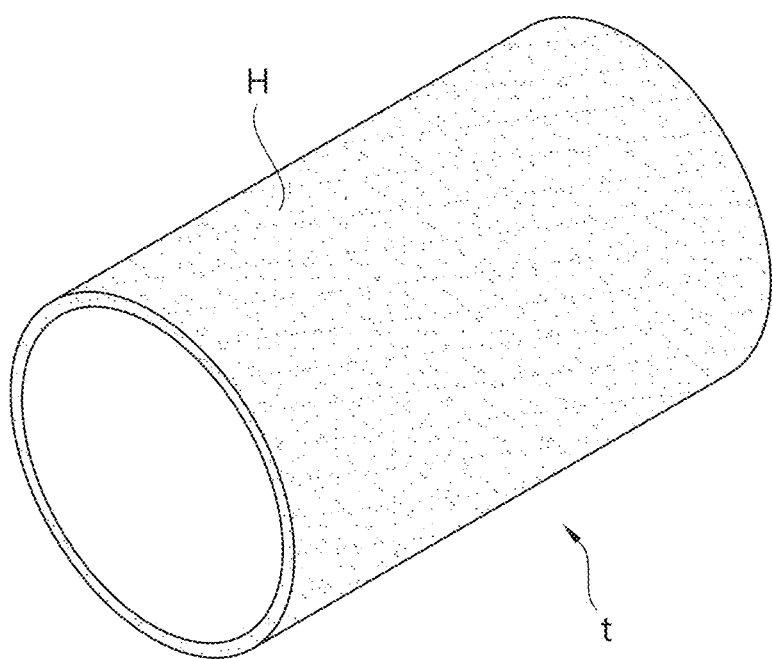
FIG. 24 illustrates a treatment region when a vaginal canal is treated using the energy transfer module for the vaginal canal treatment of FIG. 18.

The step S4240 of contracting and removing the treatment device from the vaginal canal refers to a step of contracting the treatment device and then pulling out the treatment device from the vaginal canal so that the vaginal canal can be restored to its original diameter and shape after the tissue is denatured by transmitting thermal energy to the inside of the vaginal canal FIG. 24 illustrates a treatment region when a vaginal canal is treated using the energy transfer module for the vaginal canal treatment of FIG. 18.

As shown therein, the energy transferer 301 is in contact with the inner wall of the vaginal canal and transfers the thermal energy to the vaginal canal in the state that the vaginal canal is enlarged, in which the surface heating electrodes 321 are used in transferring the thermal energy so that the tissue in the contact region can be denatured and treated.

Below, an energy transfer module for vaginal-canal treatment, a control method thereof, and a vaginal-canal treatment method using the same will be described in detail with reference to FIGS. 24 to 31. This embodiment may employ the same configuration as the foregoing embodiment, and only different configuration will be described avoiding repetitive descriptions.

Figure 25:
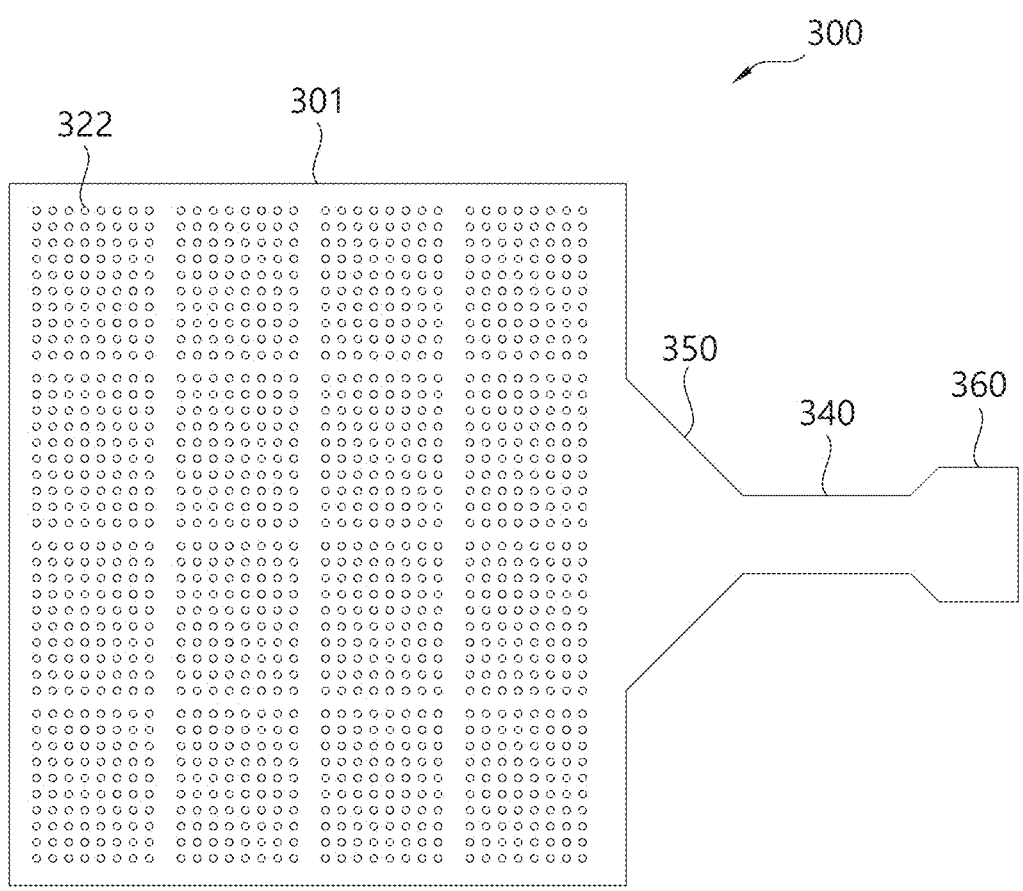
FIG. 25 is a plan view of an energy transfer module for vaginal canal treatment according to another embodiment of the disclosure.
Figure 26:
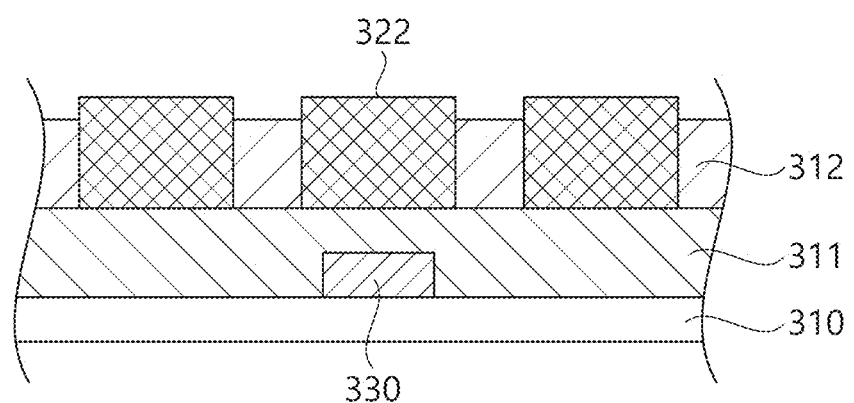
FIG. 26 is a partial cross-section view showing a partially cut-open portion of FIG. 25.

FIG. 25 is a plan view of an energy transfer module 300 for vaginal canal treatment according to another embodiment of the disclosure, FIG. 26 is a partial cross-section view showing a partially cut-open portion of FIG. 25, and FIGS. 27a, 27b and 27c illustrate alternative examples of an array of RF electrodes 322 of FIG. 25.

As shown therein, this embodiment may include RF electrodes 322. A plurality of RF electrodes 322 may be respectively provided and arrayed in the individual regions. The RF electrode 322 may be spaced apart at a predetermined distance from the adjacent RF electrode 322, thereby achieving spot heating.

Referring to FIG. 26, the plurality of RF electrodes 322 may be configured to be exposed toward the second layer 312. The RF electrode 322 is configured to receive RF power from the controller and transfer the RF power to the tissue, and configured to generate heat based on the impedance of the tissue. Therefore, the RF electrodes 322 are exposed toward the second layer 312, and, preferably, more exposed than the second layer 312 so that the RF energy can be transferred to the tissue.

The RF electrode 322 may have a smooth or plat contact surface to transfer the RF energy by a non-invasive manner when becomes in contact with the vagina inner-wall. This is to prevent the contact vagina inner-wall from being wounded when the energy transferer 301 is unrolled by the expansion of the expansion portion in the state of being inserted in the vaginal canal. Although it is described by way of example that each RF electrode 322 is shaped like a flat cylinder, this is merely an example and the RF electrode 322 may have various structures.

Figure 27A:
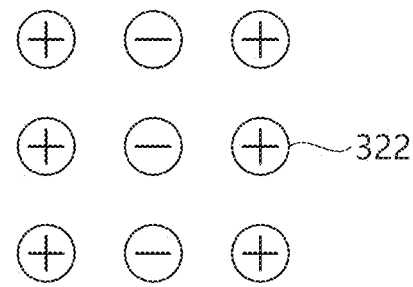
FIGS. 27a, 27b and 27c illustrate alternative examples of an array of radio frequency (RF) electrodes of FIG. 25.
Figure 27B:
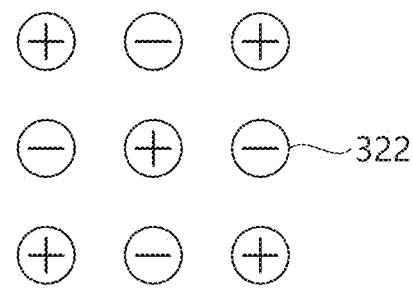
Figure 27C:
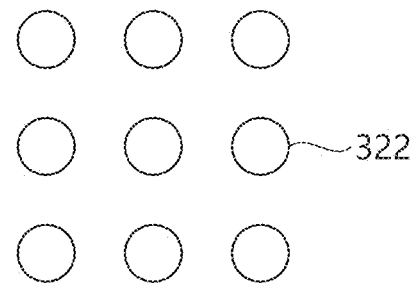

Referring to FIGS. 27a, 27b and 27c, some arrays of the RF electrodes 322 provided in each individual region are illustrated. As shown in FIGS. 27a and 27b, the RF electrode 322 may be a bipolar type. Further, as shown in FIG. 27c, the RF electrode 32 may be a monopolar type. In the case of the bipolar type, at least one of electrodes most adjacent to one RF electrode 322 may have opposite polarity. Specifically, the RF electrodes 322 may have the same polarity in one column, or different polarities may be alternated in one column. When a pair of adjacent RF electrodes 322 is in contact with the vagina inner-wall, a path of transferring the RF energy is formed via the tissue of the vagina inner-wall.

When the RF electrode 322 is the monopolar type, the arrayed electrodes may have the same polarity. In this case, a separate ground plate (not shown) may be in contact with the outside of the vaginal canal. In this case, the RF energy is transferred from the RF electrodes 322 to the tissue of the vagina inner-wall the tissue.

Meanwhile, although it is not illustrated, an electric path may be formed based on the array of the RF electrodes 322. Further, the electric path may be formed so that the individual regions can be independently controlled regardless of the types.

Below, a method of controlling the energy transfer module 300 shown in FIG. 25 will be described in detail with reference to FIG. 25.

Figure 28:
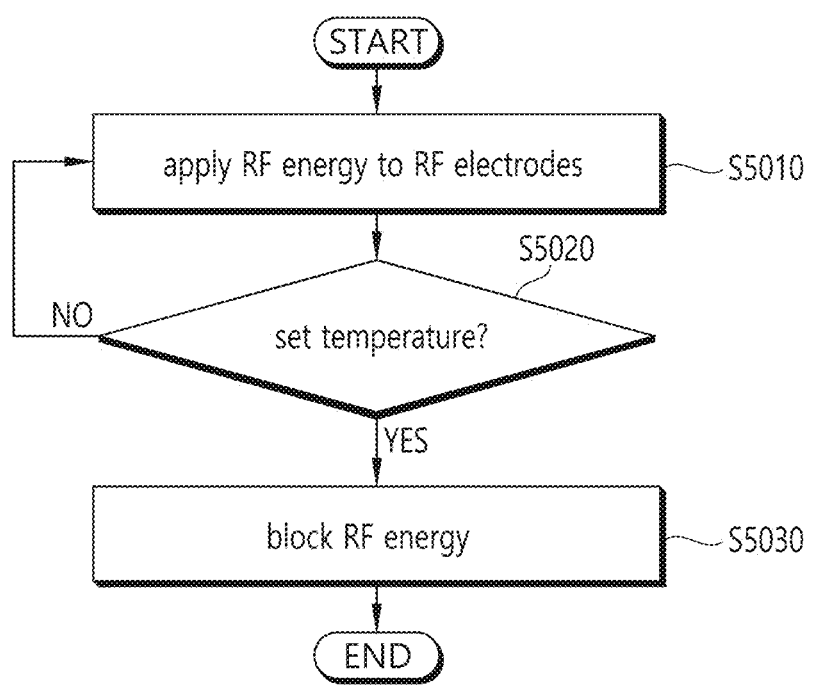
FIG. 28 is a flowchart showing a method of controlling an energy transfer module for vaginal canal treatment according to another embodiment of the disclosure.

FIG. 28 is a flowchart showing a method of controlling an energy transfer module for vaginal canal treatment according to another embodiment of the disclosure.

As shown therein, this embodiment may include an RF-energy applying step S5010, a set-temperature reaching determining step S5020, and an RF-energy blocking step S5030.

The RF-energy applying step S5010 refers to a step of applying the RF energy to the RF electrodes 322 being in contact with the vaginal canal in the state that the vaginal canal is being enlarged. The RF energy may be applied by the controller of the main body.

The set-temperature reaching determining step S5020 refers to a step of determining whether the temperature of the treatment region reaches the treatment temperature. To determine whether the temperature of the tissue reaches the set temperature, it is determined that the temperature of the vagina inner-wall reaches the set temperature selected within a rage from 60° C. to 100° C. To determine whether the temperature of the tissue reaches the set temperature, time taken in heating the temperature of a mucous membrane up to the set temperature based on the RF power is experimentally derived, and, in this case, it is determined that the temperature reaches the set temperature when the RF energy based on the RF power is applied for a predetermined period of time. In this case, a predetermined period of time, for which the RF energy is applied, may range from several microseconds to several seconds.

Meanwhile, to determine whether the temperature of the tissue reaches the set temperature, the temperature of the tissue may be estimated and determined based on an impedance value of the tissue measured by the RF electrode 322 and change in the impedance value. Further, whether the temperature of the tissue reaches the set temperature may be determined based on a measured value of the temperature sensor 330 provided in the energy transferer 301.

The RF-energy blocking step S5030 refers to a step of blocking the RF energy when it is identified that the temperature of the tissue reaches the set temperature, thereby preventing the tissue from being excessively wounded.

Figure 29:
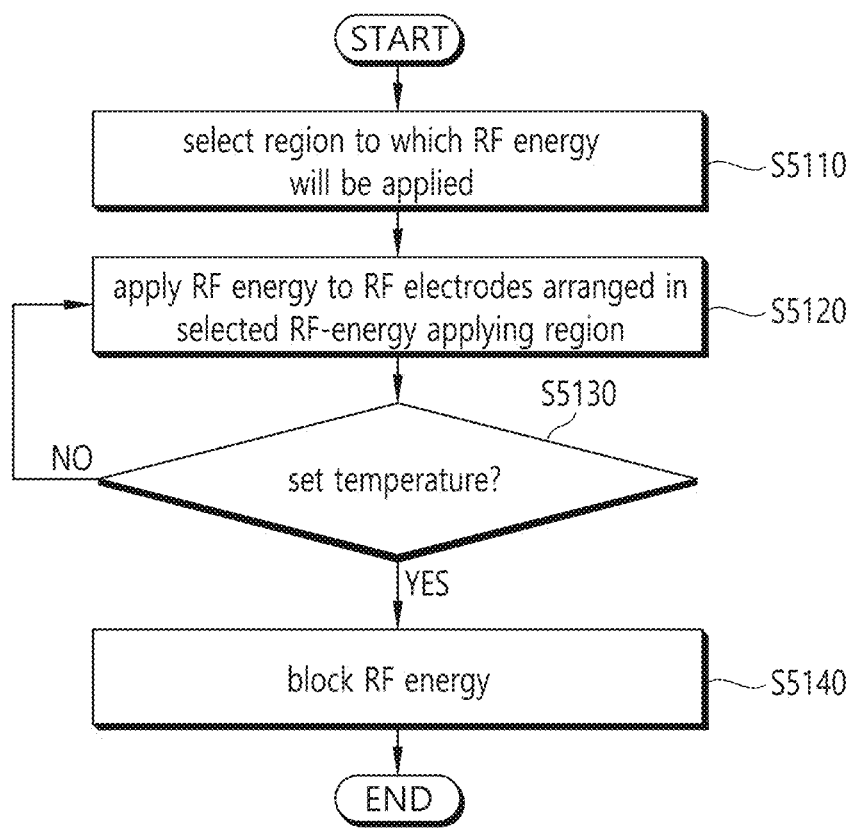
FIG. 29 is a flowchart showing a method of controlling an energy transfer module for vaginal canal treatment according to another embodiment of the disclosure.

FIG. 29 is a flowchart showing a method of controlling an energy transfer module for vaginal canal treatment according to another embodiment of the disclosure.

As shown therein, this embodiment includes an RF-energy applying region selecting step S5110, a step S5120 of applying the RF energy to the RF electrodes 322 arranged in the selected RF-energy applying region, a set-temperature reaching determining step S5130, and an RF-energy blocking step S5140.

The RF-energy applying region selecting step S5110 refers to a step of determining a region, to which the RF energy will be applied, among a plurality of individual regions. The selection of the RF-energy applying region may be based on determination of whether the region is in contact with the tissue by measuring an impedance value through the RF electrode 322. Further, the temperature sensor 330 may be used to determine whether the temperature is raised, thereby determining the contact with the tissue.

The step S5120 of applying the RF energy to the RF electrodes 322 arranged in the selected RF-energy applying region refers to a step of independently applying the RF energy to the plurality of RF electrodes 322 arranged in the selected individual region.

Below, a method of treating the vaginal canal through the energy transfer module shown in FIG. 25 will be described with reference to FIGS. 30 to 31.

Figure 30:
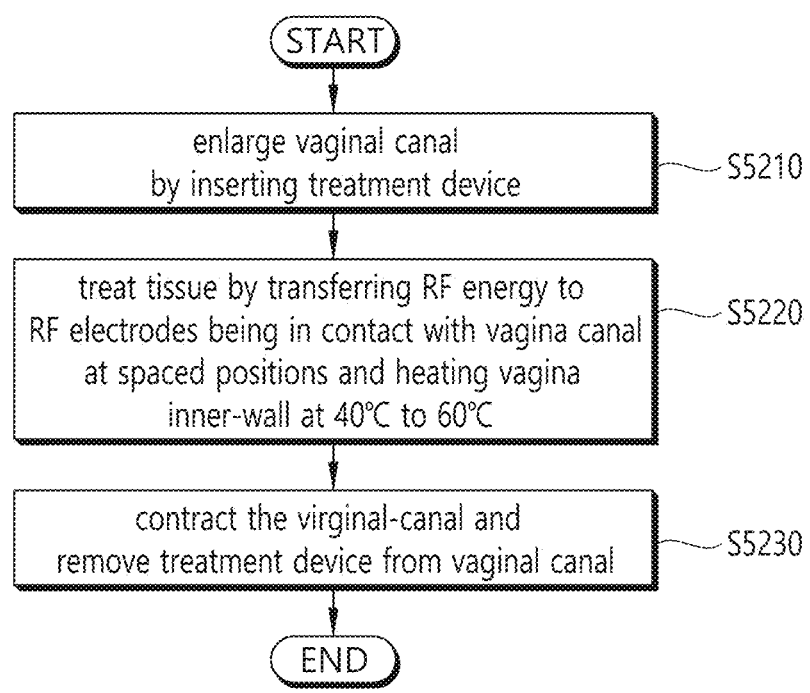
FIG. 30 is a flowchart showing a vaginal-canal treatment method using an energy transfer module for vaginal canal treatment according to another embodiment of the disclosure.

FIG. 30 is a flowchart showing a vaginal-canal treatment method using an energy transfer module 300 for vaginal canal treatment according to another embodiment of the disclosure.

As shown therein, this embodiment includes a vaginal-canal enlarging step S5210, a step S5220 of treating the tissue by heating a plurality of spaced points with the RF electrodes, and a step S5230 of contracting the virginal-canal and removing the treatment device from the vaginal canal.

Here, the vaginal-canal enlarging step S210 and the step S5230 of contracting the virginal-canal and removing the treatment device from the vaginal canal are the same as the steps S4210 and S4240 described with reference to FIG. 23, and thus repetitive descriptions will be omitted.

The step S5220 of treating the tissue by heating a plurality of spaced points with the RF electrodes refers to a step of heating the vagina inner-wall by applying the RF energy to the plurality of RF electrodes 322. This step is performed using the plurality of RF electrodes 322 being in contact with the inner wall of the vaginal canal, and the plurality of points (spots) being in contact with the RF electrode 322 undergoes the treatment. For the treatment, the RF energy is applied so that the temperature of the tissue can be raised within a range from 60° C. to 100° C. As the vagina inner-wall has a temperature of 60° C. to 100° C., cells in the tissue are denatured into an ablation state via a coagulation state, thereby carrying out the treatment. To get the ablation state, the RF energy may be transferred for several microseconds to several seconds. Meanwhile, the RF electrode 322 may be either of the bipolar type or the monopolar type.

Figure 31:
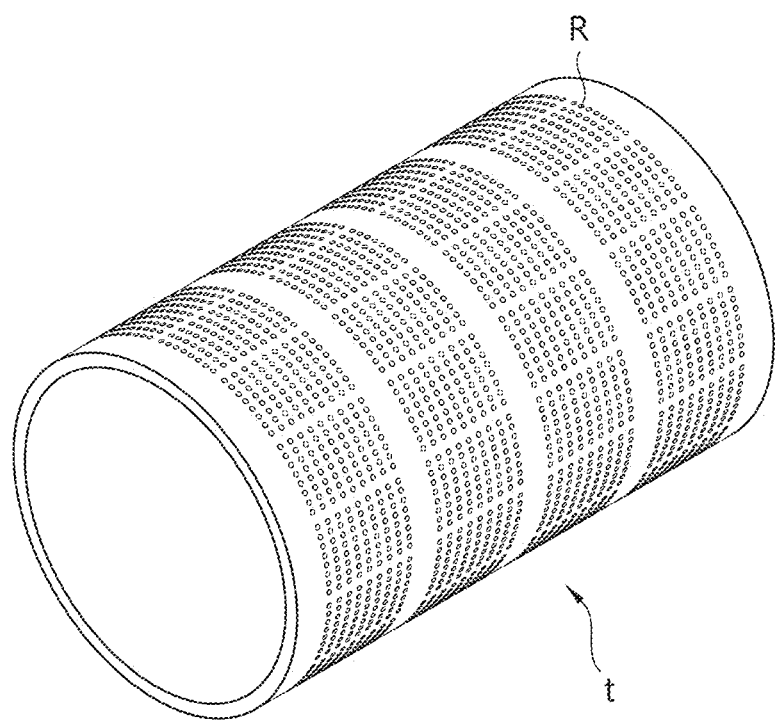
FIG. 31 illustrates a treatment region when a vaginal canal is treated using the energy transfer module for the vaginal canal treatment of FIG. 25.

FIG. 31 illustrates a treatment region when a vaginal canal is treated using the energy transfer module for the vaginal canal treatment of FIG. 25. As shown therein, the RF energy is applied to the plurality of points (R), thereby causing ablation denaturation at the plurality of points of the vagina inner-wall.

Below, an energy transfer module for vaginal-canal treatment, a control method thereof, and a vaginal-canal treatment method using the same will be described in detail with reference to FIGS. 32 to 38. This embodiment may employ the same configuration as the foregoing embodiment, and only different configuration will be described avoiding repetitive descriptions.

Figure 32:
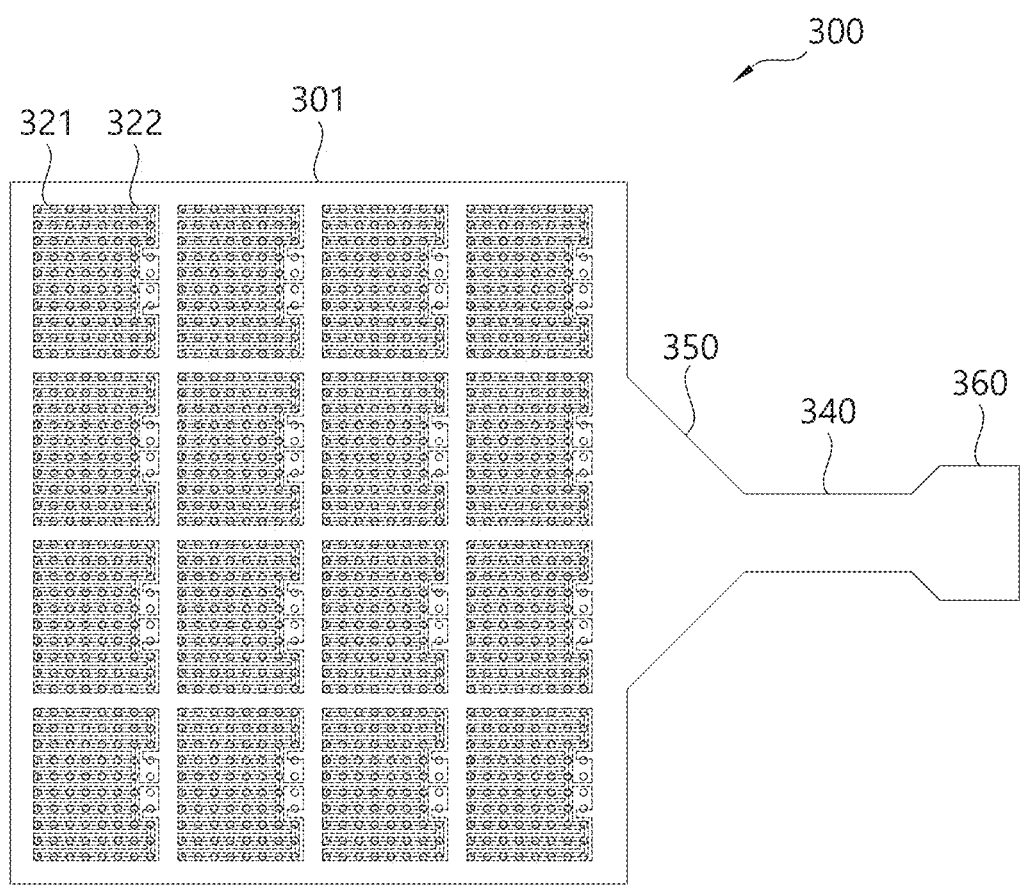
FIG. 32 is a plan view of an energy transfer module for vaginal canal treatment according to another embodiment of the disclosure.
Figure 33:
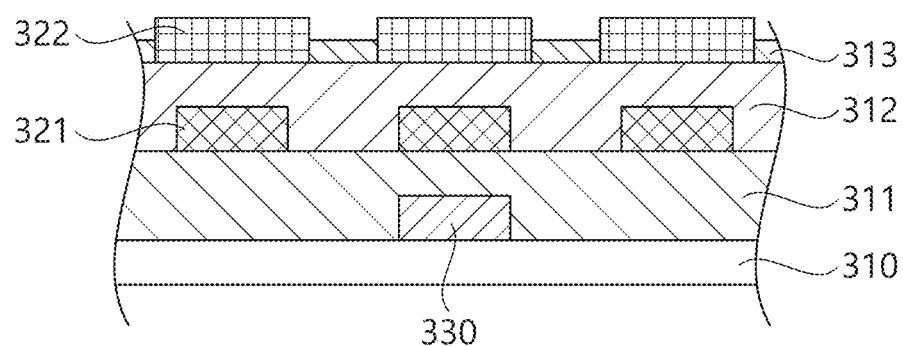
FIG. 33 is a partial cross-section view showing a partially cut-open portion of FIG. 32.

FIG. 32 is a plan view of an energy transfer module for vaginal canal treatment according to another embodiment of the disclosure, and FIG. 33 is a partial cross-section view showing a partially cut-open portion of FIG. 32.

As shown in FIG. 32, this embodiment shows heating electrodes 321 and RF electrodes 322 to perform surface heating and spot heating with regard to a plurality of divisional individual regions.

The heating electrodes 321 and the RF electrodes 322 may be overlapped to perform the spot heating in some regions where the surface heating is applied. In this case, when energy is applied to both the heating electrodes 321 and the RF electrodes 322, the coagulation denaturation generally occurs in the vagina inner-wall being in contact with one individual region, and the ablation denaturation occurs at the plurality of points (spots).

Referring to FIG. 33, this embodiment includes both the heating electrodes 321 and the RF electrodes 322, and additionally includes a third layer 313.

The heating electrodes 321 are blocked from the outside by the second layer 312 and the third layer 313 to transfer only thermal energy to the outside through self-heating.

The RF electrode 322 is provided on the top surface of the third layer 313 so as to be in direct contact with the vagina inner-wall and transfer the RF energy to the vagina inner-wall. Further, the third layer 313 is provided to insulate the RF electrodes 322 from each other.

Meanwhile, FIG. 33 illustrates an embodiment in which a heating region given in units of arraying the heating electrodes 321 and an RF-energy applying region given in units of arraying the RF electrodes 322 are overlapped, but the heating electrodes 321 and the RF electrode 322 may be arrayed to divide the regions so that an overlapped region between the heating region and the RF-energy applying region cannot be formed.

Below, a method of controlling the energy transfer module shown in FIG. 32 will be described with reference to FIGS. 34 to 35.

Figure 34:
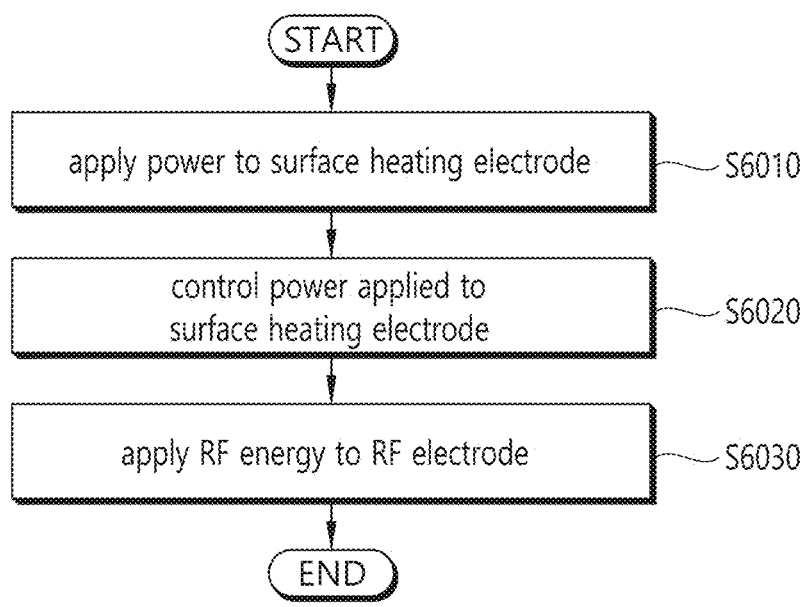
FIG. 34 is a flowchart showing a method of controlling an energy transfer module for vaginal canal treatment according to another embodiment of the disclosure.

FIG. 34 is a flowchart showing a method of controlling an energy transfer module for vaginal canal treatment according to another embodiment of the disclosure.

This embodiment includes a step S6010 of applying power to a surface heating electrode, a step S6020 of controlling the power applied to the surface heating electrode, and a step S6030 of applying RF energy to an RF electrode.

The step S6010 of applying power to the surface heating electrode refers to a step of applying power to the heating electrodes 321 so that the heating electrodes 321 can generate heat. In this step, AC power is applied so that thermal energy can be transferred to the tissue being in contact with the energy transferer 301.

The step S6020 of controlling the power applied to the surface heating electrode refers to a step of heating the vaginal inner-wall being in contact with the energy transferer 301 up to a set temperature and maintaining the temperature for a predetermined period of time so that coagulation denaturation can occur in the vagina inner-wall. The set temperature is set within a range from 40° C. to 60° C. in which coagulation occurs in the tissue, and the AC power is set not to make the temperature higher than 60° C. In this case, the set temperature may be maintained by feeding back a value measured by the temperature sensor 330 provided in the energy transfer module 300 and controlling the AC power. For example, the PWM control or the voltage control may be performed.

The step S6030 of applying RF energy to an RF electrode refers to a step of applying the RF energy to the plurality of RF electrodes 322. The step of applying the RF energy to the RF electrodes 322 is performed to cause ablation denaturation of tissue in a plurality of spot regions. In this step, the power of the RF energy may be controlled to perform the treatment under the condition that the temperature of the tissue is not higher than 100° C.

Figure 35:
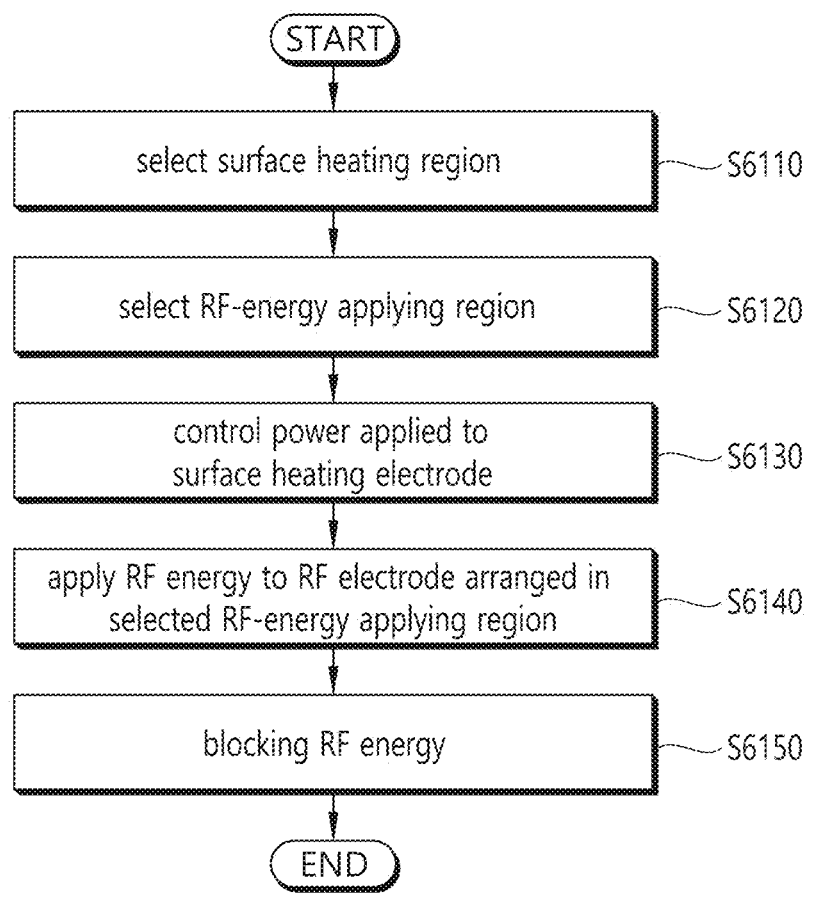
FIG. 35 is a flowchart showing a method of controlling an energy transfer module for vaginal canal treatment according to another embodiment of the disclosure.

FIG. 35 is a flowchart showing a method of controlling an energy transfer module for vaginal canal treatment according to another embodiment of the disclosure.

As shown therein, this embodiment may further include a surface-heating region selecting step S6110, and an RF-energy applying region selecting step S6120.

The surface-heating region selecting step S6110 refers to a step of selecting a region, to which energy will be applied, among the surface heating electrodes 321. This step may be set based on a user's input, and the selection may be made with regard to a determined region with which the vagina inner-wall is in contact among the plurality of surface heating regions.

The RF-energy applying region selecting step S6120 refers to a step of selecting a region, to which the RF energy will be applied, among the plurality of RF-energy applying regions, and the selection may be made based on a user's selection or an algorithm involved in the controller, like the surface-heating region selecting step S6110

Meanwhile, the surface-heating region and the RF-energy applying region may be selected independently of each other, may be differently selected, or may be equally selected.

Meanwhile, this embodiment shows an example that a step S6130 of applying power to the surface heating electrode is first performed, and a step S6140 of applying the RF energy to the RF electrode is then performed. However, such two steps may be performed reversely or simultaneously.

Below, a vaginal-canal treatment method using the energy transfer module 300 shown in FIG. 32 will be described with reference to FIGS. 36 to 38.

Figure 36:
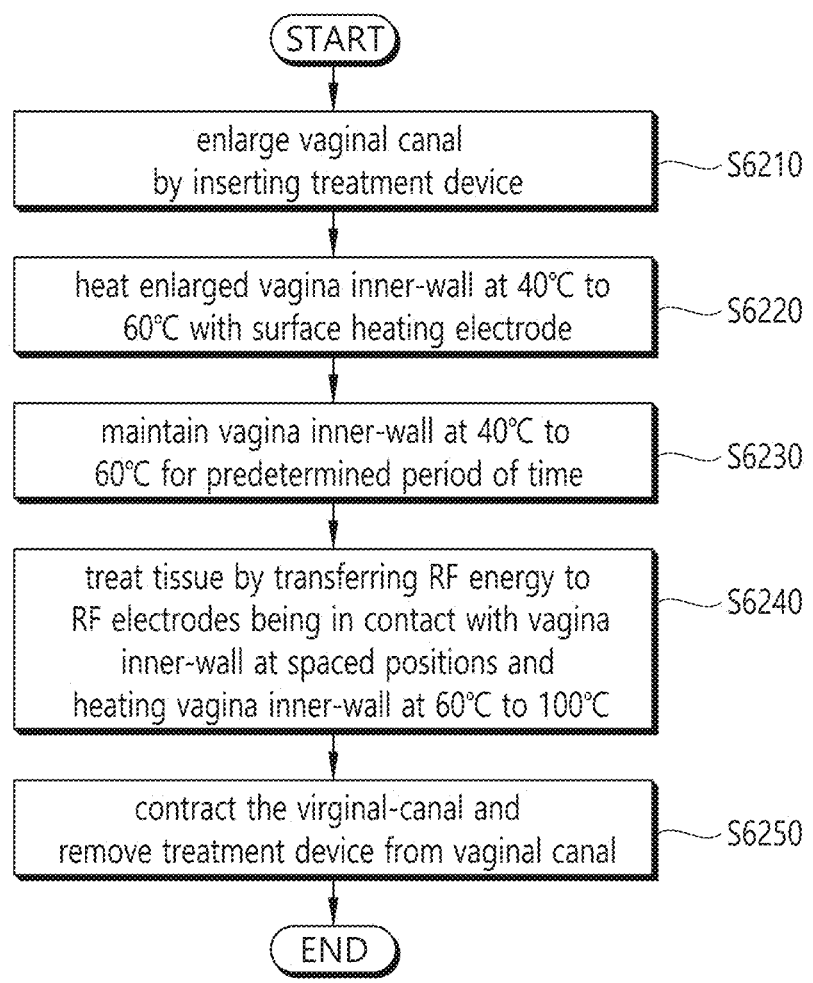
FIG. 36 is a flowchart showing a vaginal-canal treatment method using an energy transfer module for vaginal canal treatment according to another embodiment of the disclosure.

FIG. 36 is a flowchart showing a vaginal-canal treatment method using an energy transfer module 300 for vaginal canal treatment according to another embodiment of the disclosure. In this embodiment, a vaginal-canal enlarging step 6210 and a step S6250 of contracting the virginal-canal and removing the treatment device from the vaginal canal are the same as the steps S4210 and S4240 described with reference to FIG. 23, and thus repetitive descriptions will be omitted.

As shown therein, this embodiment may include a step S6220 of heating the enlarged vagina inner-wall at 40° C. to 60° C. by the surface heating electrodes 321 after the vaginal-canal enlarging step 6210, a step S6230 of maintaining the vagina inner-wall at 40° C. to 60° C. for a predetermined period of time, and a tissue treatment step S6240 of transferring the RF energy to the RF electrodes being in contact with the vagina inner-wall at a plurality of spaced points and heating the vagina inner-wall at 60° C. to 100° C.

The step S6220 of heating the enlarged vagina inner-wall at 40° C. to 60° C. by the surface heating electrodes 321 and the step S6230 of maintaining the vagina inner-wall at 40° C. to 60° C. for a predetermined period of time may be performed equally to the steps S4220 and S4230 described with reference to FIG. 23.

The tissue treatment step S6240 of transferring the RF energy to the RF electrodes being in contact with the vagina inner-wall at a plurality of spaced points and heating the vagina inner-wall at 60° C. to 100° C. may be performed equally to the step S5220 described with reference to FIG. 30.

Figure 37:
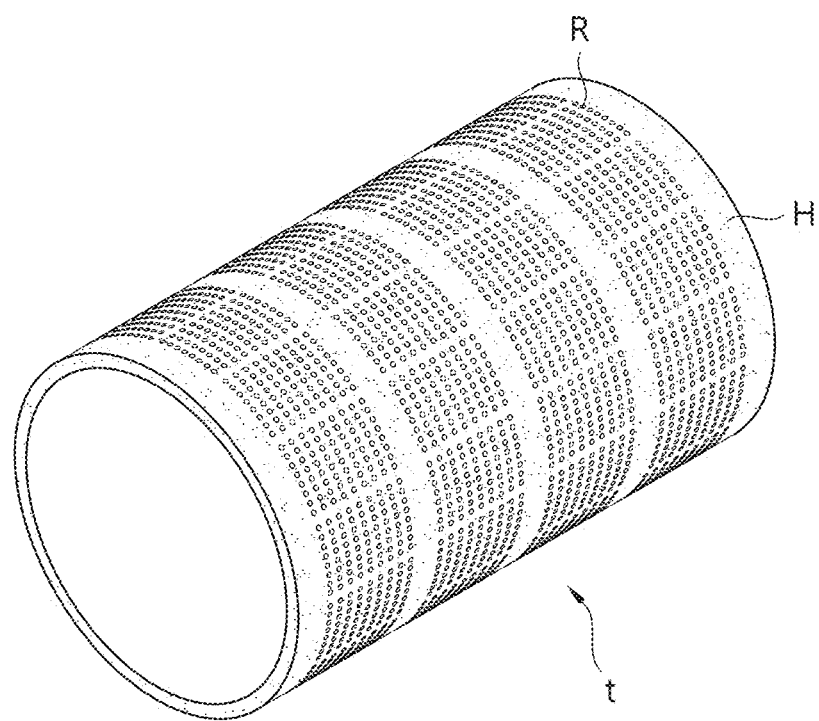
FIG. 37 illustrates a treatment region when a vaginal canal is treated using the energy transfer module for the vaginal canal treatment of FIG. 32.

FIG. 37 illustrates a treatment region when a vaginal canal is treated using the energy transfer module 300 for the vaginal canal treatment of FIG. 32. This embodiment is implemented in the state that the vagina inner-wall is enlarged, so that coagulation denaturation can occur in most of regions and ablation denaturation can occur at plurality of spots overlapped with the regions, thereby causing different denaturation according to parts.

FIG. 38 is a graph showing temperature profile corresponding to portions when electrode treatment is performed using the energy transfer module 300 for the vaginal canal treatment of FIG. 32. FIG. 38 shows a portion of the energy transfer module 300 and the vagina inner-wall being in contact with the energy transfer module 300. This embodiment shows an example that a coagulation region and an ablation region are overlapped. A point T1 and a point T2 are heated at 60° C. by the surface heating and then the temperature is maintained for a predetermined period of time. The treatment based on the surface heating takes much more time than that based on the RF-energy transferring because the heating is achieved by heat transfer based on difference in temperature between the vagina inner-wall and the heating electrodes 321. Therefore, the tissue is first heated by the surface heating at 60° C. and maintained for a predetermined period of time to result in coagulation denaturation. Then, the RF electrodes 322 transfer the RF energy to some points T2 and perform heating up to 100° C. for a short period of time, thereby resulting in ablation.

Meanwhile, this embodiment shows an example that ablation denaturation at a plurality of points within the coagulation denaturation region, but the coagulation denaturation region and the ablation denaturation region may be selected as a partially overlapped region or a not-overlapped region and undergo treatment. Further, although it is described by way of example that the coagulation denaturation first occurs and then the ablation denaturation occurs, the ablation denaturation may first occur or ablation denaturation may occur during the coagulation denaturation.

As described above, the disclosure provides an energy transfer module for a vaginal-canal treatment device, a control method thereof, and a treatment method using the same, in which energy is transferred by insertion into a vaginal canal and enlargement of the vaginal canal to thereby perform treatment by selectively or complexly causing ablation and coagulation denaturation in a large area for a short period of time, and one-shot treatment is possible and wrinkled part can undergo the treatment to thereby improve the treatment in efficiency and accuracy. Further, the tissue in the vaginal canal is treatable without a surgical operation, thereby having an effect on minimizing a patient's suffering or discomfort.

The invention claimed is:
1. An energy transfer module for vaginal canal treatment, the module comprising:
a flexible substrate configured to be transformed as an expansion element for enlarging a vaginal canal is expanded so that the vaginal canal is unwrinkled, the expansion element having a closed distal end portion and a body portion, the body portion having a cylindrical shape; and a heating electrode provided on the flexible substrate and configured to generate heat to heat the vaginal canal, wherein the flexible substrate has a quadrangular plate shape, is arranged to roll up in a circumferential direction of the body portion of the expansion element, and gradually unrolls, increasing an area of its outer surface that corresponds to an area of the heating electrode in contact with the vaginal canal as the expansion element expands, wherein the heating electrode comprises a plurality of heating electrodes, wherein the flexible substrate comprises a first insulating layer and a second insulating layer which are configured to be in at least partially contact with the vaginal canal, and the plurality of heating electrodes are provided between the first insulating layer and the second insulating layer.

2. The energy transfer module of claim 1, wherein the heating electrode is configured to generate the heat throughout a surface.

3. The energy transfer module of claim 1, wherein each heating electrode is provided in each individual region divided on a plane of the flexible substrate, and each heating electrode is configured to independently heat each individual region.

4. The energy transfer module of claim 3, wherein the heating electrode is configured to receive alternating current (AC) power and generate the heat.

5. The energy transfer module of claim 3, further comprising a temperature sensor configured to measure temperature corresponding to heating of the heating electrode.

6. The energy transfer module of claim 5, wherein the temperature sensor is provided in the second insulating layer.

7. The energy transfer module of claim 1, wherein the heating electrode has a stripe shape that extends in the circumferential direction.

8. A method of controlling an energy transfer module for vaginal canal treatment, the method comprising:

enlarging a vaginal canal by expanding an expansion element;

applying power to generate heat from a heating electrode provided on a substrate, the heating electrode being in contact with a vagina inner-wall as the expansion element expands so that the vaginal canal is unwrinkled; and controlling power to maintain the vagina inner-wall at a set temperature for a set period of time, wherein the expansion element has a closed distal end portion and a body portion, the body portion having a cylindrical shape, and wherein the substrate has a quadrangular plate shape, is arranged to roll up in a circumferential direction of the body portion of the expansion element, and gradually unrolls to increase an area of its outer surface that corresponds to an area of the heating electrode in contact with the vagina inner-wall as the expansion element expands.

9. The method of claim 8, wherein the heating electrode is configured to generate heat throughout a surface, the heating electrode comprises a plurality of heating electrodes which are respectively provided in a plurality of regions divided from the substrate, and the applying of the power comprises applying power to a heating region selected among the plurality of regions based on a preset mode or a user's input.

10. The method of claim 9, wherein the applying of the power comprises controlling power by feeding back a temperature measurement value from a temperature sensor provided in the substrate.

11. The method of claim 10, wherein the applying of the power comprises performing pulse width modulation (PWM) by feeding back the temperature measurement value.

12. The method of claim 10, wherein the applying of the power comprises adjusting voltage of the power by feeding back the temperature measurement value.

13. The method of claim 10, wherein the applying of the power comprises controlling the power to maintain the temperature measurement value at a set temperature of 40° C. to 70° C.

14. A vaginal-canal treatment method using an energy transfer module for vaginal canal treatment, the vaginal-canal treatment method comprising:

enlarging a vaginal canal to be unwrinkled by inserting a treatment device comprising a heating electrode provided on a substrate into an opening of the vaginal canal and expanding an expansion element of the treatment device;

treating tissue by heating an inner wall of the enlarged vaginal canal with the heating electrode; and removing the treatment device, wherein the expansion element has a closed distal end part and a body portion, the body portion having a cylindrical shape, and wherein the substrate has a quadrangular plate shape, is arranged to roll up in a circumferential direction of the body portion of the expansion element, and gradually unrolls to increase an area of its outer surface that corresponds to an area of the heating electrode in contact with the inner wall of the enlarged vaginal canal as the expansion element expands.

15. The vaginal-canal treatment method of claim 14, wherein the treating of the tissue is performed by transferring thermal energy from the heating electrode to the inner wall of the vaginal canal.

16. The vaginal-canal treatment method of claim 15, wherein the treating of the tissue is performed by heating at least a part divided from a treatment region of the inner wall of the vaginal canal.

17. The vaginal-canal treatment method of claim 15, wherein the treating of the tissue comprises causing coagulation denaturation in tissue of a treatment region.

18. The vaginal-canal treatment method of claim 17, wherein the treating of the tissue comprises performing treatment for one or more of tightening, rejuvenation, laxity, lifting, and tone and textural changes of the inner wall of vaginal canal.

19. The vaginal-canal treatment method of claim 14, wherein
the treating of the tissue comprises maintaining a treatment region at 40° C. to 60° C. for a predetermined period of time.

* * * * *